United States Patent [19]

Arai et al.

[11] Patent Number: 5,757,659
[45] Date of Patent: May 26, 1998

[54] AUTOMATIC ANALYSIS SYSTEM

[75] Inventors: Toyofumi Arai, Ama-gun; Akira Narukawa, Yokkaichi, both of Japan

[73] Assignee: NGK Insulators, Ltd., Japan

[21] Appl. No.: 624,808

[22] Filed: Mar. 27, 1996

[30] Foreign Application Priority Data

Mar. 27, 1995 [JP] Japan .............. PCT/JP95/563

[51] Int. Cl.$^6$ .................................................. G01N 35/00
[52] U.S. Cl. .................. 364/497; 364/496; 364/468.22; 364/468.23; 436/43; 436/56; 436/52; 422/62; 422/63; 235/375; 235/380
[58] Field of Search .......................... 364/496, 497, 364/468.22, 468.23, 481, 921.8, 949.5; 422/62, 63, 67; 436/43, 46–47, 50–52, 56; 235/375, 380, 487, 493, 58 R, 85 R

[56] References Cited

U.S. PATENT DOCUMENTS

| | | | |
|---|---|---|---|
| 4,158,545 | 6/1979 | Yamashita et al. | 436/47 |
| 4,460,824 | 7/1984 | Kadogaki | 235/375 |
| 4,678,752 | 7/1987 | Thorn et al. | 435/287.3 |
| 5,051,238 | 9/1991 | Umetsu et al. | 422/64 |
| 5,100,622 | 3/1992 | Mimura et al. | 422/67 |
| 5,104,621 | 4/1992 | Pfost et al. | 422/67 |
| 5,314,825 | 5/1994 | Weyrauch et al. | 436/43 |
| 5,321,619 | 6/1994 | Matsuda et al. | 364/468.23 |
| 5,357,095 | 10/1994 | Weyrauch et al. | 235/494 |
| 5,420,408 | 5/1995 | Weyrauch et al. | 235/454 |
| 5,437,024 | 7/1995 | French | 395/610 |

FOREIGN PATENT DOCUMENTS

| | | |
|---|---|---|
| 52-10192 | 1/1977 | Japan . |
| 59-116046 | 7/1984 | Japan . |
| 4-113071 | 10/1992 | Japan . |
| 5-142232 | 6/1993 | Japan . |

OTHER PUBLICATIONS

"Routine Analysis Control by Data Base System", Analytical Chemistry, vol. 37, No. 11 (1988) (Japanese Analytical Chemistry Society.

"Trial of Laboratory Automation for Chemical Experiment (Medical Density Measurement) Business", Interface, No. 7 (1988).

"New Analysis System in Mizushima Factory", Shimazu Chemical Machinery and Tools News, vol. 28, No. 2 (1987).

"Chemical Component Analyzing Computer System", Mitsubishi Seiko Giho, vol. 22, No. 1–2 (1988).

Primary Examiner—Emanuel T. Voeltz
Assistant Examiner—Tuan Q. Dam
Attorney, Agent, or Firm—Parkhurst & Wendel

[57] ABSTRACT

An automatic analysis system comprising analytical equipment and a host computer connected to the analytical equipment. The host computer assigns identification numbers to pieces of analysis information, respectively, further assigns identification numbers to the pieces of analysis information respectively, to relate the pieces of analysis information to each other, groups a predetermined number of the pieces of analysis information to form pieces of group information, assigns identification numbers to the pieces of group information, respectively, further groups a predetermined number of the pieces of group information to form pieces of group information, and then assigns identification numbers to the pieces of group information, respectively. A storage device is provided for storing the pieces of analysis information and group information to which the identification numbers are given by the host computer. The host computer further retrieves the pieces of analysis information and group information stored in the storage means, reads same in a mutually related manner, processes and edits same. An arrangement form or the final results edited by the control means are output by output means. According to this automatic analysis system, a chemical analysis test can be promptly and efficiently processed and artificial errors scarcely occur, so that the test results having an extremely high reliability can be reported.

35 Claims, 24 Drawing Sheets

Example of main menu

FIG. 12

Example of chemical analysis request form

| Request form number | OOOOOOO | Request date | month day, year |
|---|---|---|---|
| Requester name | Ichiro Higai | Requester's belonging section | Engineering Section |
| Desired due date | month day, year | | |

| Analytical measurement test sample name | Analytical measurement test item name |
|---|---|
| Sample name 1 | Test item name 1  Test item name 2  Test item name 3  Test item name 4  Test item name 5 · · · · · |
| Sample name 2 | Test item name 1  Test item name 2  Test item name 3  Test item name 4  Test item name 5 · · · · · |
| · · · · · | · · · · · |

Special mention on analysis request

FIG. 13

Example of arrangement form for loss-on-ignition measurement

Output date and time:
Month day, year, hr min

Output page / total number of pages

| Request number | Analytical measurement sample name | Analytical measurement test sample group identification number | Analysis due date | Ignition temperature | Type of crucible | Instruction |
|---|---|---|---|---|---|---|
| Request number 1 | Sample name 1 | OOOOOOOO | month day, year | OOOO | OO | OOOOOOOOOOOOOOOO |
|  | Sample name 2 | OOOOOOOO | month day, year | OOOO | OO |  |
|  | Sample name 3 | OOOOOOOO | month day, year | OOOO | OO | OOOOOOOOOOOOOOOO |
| Request number 2 | Sample name 1 | OOOOOOOO | month day, year | OOOO | OO |  |
|  | Sample name 2 | OOOOOOOO | month day, year | OOOO | OO |  |

FIG. 14

Example of report on chemical analysis results (1)

Report date,
Name of department
in charge of analysis

| Request form number | ○○○○○○○ | | |
|---|---|---|---|
| Requester name | Ichiro Higai | | |
| Number of analytical measurement test samples | ○○ | Number of analytical measurement test items | ○○ |
| Cost of analytical measurement test | ○○○○ yen | | |

Analytical measurement
                              test sample name 1

| Analytical measurement test item name 1 | Analytical measurement test value 1 | Unit name of analytical measurement test value 1 |
| Analytical measurement test item name 2 | Analytical measurement test value 2 | Unit name of analytical measurement test value 2 |
| Analytical measurement test item name 3 | Analytical measurement test value 3 | Unit name of analytical measurement test value 3 |
| Analytical measurement test item name 4 | Analytical measurement test value 4 | Unit name of analytical measurement test value 4 |

·                    ·
            ·     Analytical measurement   ·
            ·     test sample name 2    ·

| Analytical measurement test item name 1 | Analytical measurement test value 1 | Unit name of analytical measurement test value 1 |
| Analytical measurement test item name 2 | Analytical measurement test value 2 | Unit name of analytical measurement test value 2 |
| Analytical measurement test item name 3 | Analytical measurement test value 3 | Unit name of analytical measurement test value 3 |
| Analytical measurement test item name 4 | Analytical measurement test value 4 | Unit name of analytical measurement test value 4 |

Consideration and remarks on analytical measurement test results

Output date and time :
month day, year, hr min

Output page,
Total number of pages

FIG. 16

Arrangement form for wet chemical analysis

Acceptance date : month day, year to month day, year
Output date and time : month day, year, hr min Output page, Total number of pages

| Request number | Customer name | Analytical measurement test sample identification number | Analytical measurement test sample name | Analysis due date | Priority | Name of person in charge of analysis | Analytical measurement test method name | Analytical measurement test item name | Comment |
|---|---|---|---|---|---|---|---|---|---|
| Request number 1 | Customer name 1 | ooooooo | Sample name 1 | month day, year | oo | Name of person in charge 1 | Test method name 1<br>Test method name 2 | Test item name 1<br>Test item name 2 | |
| | | ooooooo | Sample name 2 | month day, year | oo | Name of person in charge 2 | Test method name 1 | Test item name 1 | |
| | | | | | | Name of person in charge 1 | Test method name 1<br>Test method name 2 | Test item name 1<br>Test item name 2 | |
| | | | | | | Name of person in charge 2 | Test method name 1 | Test item name 1 | |
| | | | | | | Name of person in charge 3 | Test method name 1<br>Test method name 2 | Test item name 1<br>Test item name 2 | |
| | | ... | ... | ... | ... | ... | ... | ... | |
| Request number 2 | Customer name 2 | ooooooo | Sample name 1 | month day, year | oo | Name of person in charge 1 | Test method name 1<br>Test method name 2 | Test item name 1<br>Test item name 2 | |
| ... | ... | | ... | ... | | | | | |

Monthly transition of number of analytical measurement test samples

Rate of number of analytical measurement test samples for each request department

AUTOMATIC ANALYSIS SYSTEM

BACKGROUND OF THE INVENTION AND RELATED ART

The present invention relates to an automatic analysis system which is automated in the range of from acceptance to report of an analytical measurement test operation. The analytical measurement test operation includes a chemical analysis test, a material test and the like. Hereinafter, a chemical analysis test operation will be described in detail.

It is extremely important for a quality control operation, a process control operation, and a research development operation of products and materials in various industries to analyze the compositions and characteristics of many chemical samples and to provide analysis data having a high reliability.

The above-mentioned analysis operation has been computerized/automated so far in order to quickly carry out a test and provide analysis data with a high reliability, and for example, some relevant techniques have been suggested in Japanese Utility Model Application Laid-open No. 113071/1992 as well as Japanese Patent Application Laid-open Nos. 116046/1984, 142232/1993 and 10192/1977.

However, in the above-mentioned conventional computerized and automated analysis operation, much attention has been paid to the automation of the pretreatment and measurement of a sample as well as data processing necessary for an analytical equipment, but there have not been presently considered the acceptance and entry of the sample to be analyzed, analysis preparation, analysis progress control, and the preparation of an analytical result report in which analysis data from each analytical equipment are combined.

Specifically, Japanese Utility Model Application Laid-open No. 113071/1992 has described a connector for directly connecting an analytical equipment to a general-purpose network, and data processing for an analytical equipment regarding an equipment identification number input unit. That is to say, it is described herein that an identification number is given to identify equipment, but this conception is not an art for giving an identification number to each piece of analysis information.

Japanese Patent Application Laid-open No. 116046/1984 relates to a method for identifying a specimen group in a continuous analytical measurement test. In this method, a data track address of a floppy disk is used as an identification number for the sequence of storing information in a storage unit (e.g., the floppy disk) or the coordination of a physical storage position with analysis information, but the disclosed method is not a technique which comprises separately giving an identification number to each piece of analysis information to group the pieces of the analysis information, further grouping the pieces of group information from a predetermined viewpoint, and then giving an identification number to the group.

Moreover, Japanese Patent Application Laid-open No. 142232/1993 relates to a clinical-inspection specimen sorting system which inquires of a host system with an identification number peculiar to a specimen. The host system is provided with a function for giving a treatment or the like corresponding to a requested item. That is to say, Japanese Patent Laid-Open No. 142232/1993 has described giving an identification number and inquiring information with an identification number, but this publication does not disclose an art for individually giving an identification number to each piece of analysis information, grouping the pieces of analysis information, and further grouping the groups of analysis information from a predetermined viewpoint and giving an identification number to each group.

Furthermore, Japanese Patent Application Laid-open No. 10192/1977 relates to a method for preparing a report on analysis and test of harmful substances and discloses a format for entering test results including all the analysis and test items. However, the official gazette does not disclose art for individually giving an identification number to each piece of analysis information, grouping them, and further grouping the groups of analysis information from a predetermined viewpoint and giving an identification number to each group.

Therefore, the present inventors have previously proposed the so-called unitary analysis information control system by which the analysis information of from the acceptance/entry of an analysis sample to the preparation of an analytical result report necessary to carry out daily analysis operations in "Routine Analysis Control by Data Base System", Analytical Chemistry, Vol. 37, No. 11, (1988) (Japanese Analytical Chemistry Society) can be immediately provided when requested by an analyst. This unitary analysis information control system is a data processing system in which a plurality of analytical measurement test equipments are connected to a computer, and analytical measurement test data are collected, processed and edited, and the results are then output.

This unitary analysis information control system has, for example, (1) an effect that the simple errors of the analysis due to immatureness and carelessness and the transfer errors of the analysis data can be decreased, so that the reliability of the analysis data can be improved, (2) an effect that the analysis results can be quickly reported, and (3) an effect that the processing system of a routine analysis operation can be simplified.

However, this system cannot output a final report of a format which can be sent to a customer, because the system does not unitarily control a lower limit value of determination, an error, an analysis accuracy, a unit and the like of an analytical measurement test every item of customer information, analytical measurement test sample information and an analytical measurement test.

Thus, the present invention intends to further improve the above-mentioned conventional systems, and an object of the present invention is to provide an automatic analysis system which can realize high-speed processing and can expand information to be unitarily processed.

SUMMARY OF THE INVENTION

That is to say, according to the first aspect of the present invention, there is provided an automatic analysis system which comprises an analytical equipment and a host computer connected to the analytical equipment, said host computer comprising control means for giving identification numbers for identification to pieces of analysis information such as an analytical measurement test sample name, an analytical measurement test item name, an analytical measurement test method name, an analytical measurement tester name, an analytical measurement test requester, i.e., a customer name as well as lower limit values, errors, analysis accuracies and units of an analytical measurement test, respectively, further giving identification numbers to the pieces of analysis information, respectively, to relate the pieces of analysis information to each other, grouping a predetermined number of the pieces of analysis information to form pieces of group information, giving identification numbers to the pieces of group information, respectively, further grouping a predetermined number of the pieces of group information to form pieces of group information, and then giving identification numbers to the pieces of group information, respectively, and storage means for storing the pieces of analysis information and group information to which the identification numbers are given by the control means.

According to the second aspect of the present invention, there is provided an automatic analysis system which comprises an analytical equipment and a host computer connected to the analytical equipment, said host computer comprising control means having functions of giving first identification numbers to pieces of analysis information, respectively, to mutually identify the pieces of analysis information and to relate the pieces of analysis information to each other, grouping a predetermined number of the pieces of analysis information to form pieces of first group information, giving second identification numbers to the pieces of first group information, respectively, further grouping the pieces of first group information in accordance with a predetermined viewpoint to form pieces of second group information, and then giving third identification numbers to the pieces of second group information, respectively, and storage means for storing the pieces of analysis information to which the first, second and third identification numbers are given by the control means.

Moreover, in the present invention, the respective pieces of analysis information are grouped in accordance with a common attribute to form the first group information, and the respective pieces of analysis information are grouped in accordance with the property or purpose of the respective pieces of analysis information such as a chemical composition, an analytical measurement test method or an analytical result report preparation method to form the second group information. Furthermore, the identification numbers are given to the pieces of the first and second group information, and these pieces of the information are then stored, whereby the handling of the information can be preferably improved.

In the present invention, the respective pieces of analysis information basically comprise measured data and relevant information other than the measured data, and to these pieces of analysis information, identification numbers are given. Then, they are stored in storage means. These pieces of analysis information are retrieved by the control means, read in a mutually related manner, processed and then edited, and the final results are output by output means such as a printer.

Furthermore, in present invention, the respective pieces of analysis information necessary for an analytical measurement test such as a test item, a test sequence, a test method and test conditions are read from the storage means prior to the execution of the analytical measurement test, and these pieces of analysis information are output as an arrangement document, whereby artificial errors can be prevented and the analytical measurement test can be correctly and smoothly carried out.

Moreover, in the middle stage of the analytical measurement test, the analysis progress state is read out from the storage means, whereby reference can be made and the control of the analytical measurement test can be accurately and quickly accomplished. In addition, the efficiency of the analytical measurement test can be improved.

BRIEF DESCRIPTION OF THE DRAWINGS

FIG. 12 shows a chemical analysis request form.

FIG. 13 shows an arrangement form.

FIG. 14 shows a chemical analysis result report.

FIG. 16 shows an arrangement form.

FIG. 20 shows "acceptance information" as one example of relating and grouping the respective pieces of analysis information.

FIG. 21 shows "analytical measurement test information" as one example of relating and grouping the respective pieces of analysis information.

FIG. 22 shows "arrangement form information" as one example of relating and grouping the respective pieces of analysis information.

FIG. 24 shows "analysis result report information" as one example of relating and grouping the respective pieces of analysis information.

DETAILED DESCRIPTION OF THE INVENTION

Figure 1:
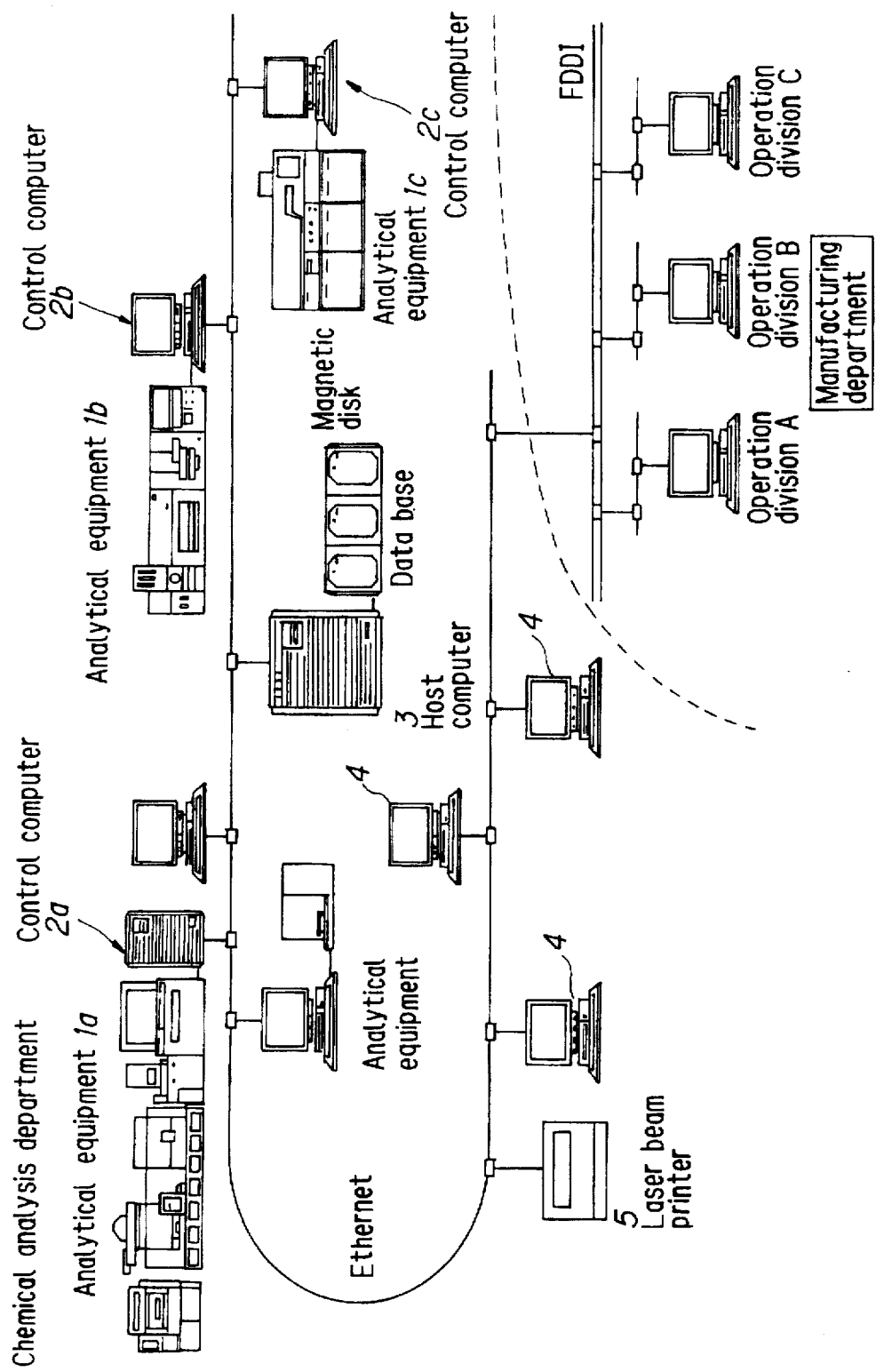
FIG. 1 is a whole schematic block diagram of an automatic analysis system.

In the present invention, it is preferred that pieces of analysis information such as customer names, analytical measurement tester names, analytical measurement test names, analytical measurement test methods, and lower limit values, errors, analysis accuracies and units of analytical measurement tests are grouped in accordance with common attributes. For example, first identification numbers are given to pieces of analysis information to identify the pieces of analysis information constituting the first group information of customer information, analytical measurement test sample information, measured data information, analytical measurement test item information and the like and to identify the mutual relations between the pieces of analysis information. In addition, second identification numbers are given to the pieces of the first group information to identify them, and they are then stored in the storage means of a host computer. In this case, the first identification numbers are given to the respective pieces of analysis information, for example, the respective test samples by the control means of the host computer. Furthermore, for example, in the case of a use purpose such as the preparation of an analysis result report, the pieces of the first group information are grouped in accordance with predetermined viewpoints to form the second group information of, for example, analysis result report information. Next, third identification numbers are given to the group names of the second group information, and they are then stored. This procedure is preferable for easy handling and high-speed processing.

Moreover, it is preferred that the grouping of the respective pieces of analysis information can be achieved by forming groups in a multistage manner, and for example, the respective pieces of analysis information are grouped, and the obtained pieces of group information are further grouped to form group information, whereby the processing efficiency of the information can be improved.

In an automatic analysis system of the present invention, the respective pieces of analysis information basically comprise measured data and relevant information other than the measured data, and to these pieces of analysis information, identification numbers are given. Then, they are stored in storage means. These pieces of analysis information and the group information are retrieved, read out in a mutually related manner, processed and then edited by the control means, and the final results are output by output means such as a printer.

The above-mentioned relevant information usually comprises the customer information of the first group information including at least customer names and the analytical measurement test sample information of the first group information including at least analytical measurement test sample names. Here, the analytical measurement test sample information of the first group information is related to the analytical measurement test item information of the first group information recognized by an analytical measurement test sample group identification number of the first identification numbers included in the analytical measurement test sample information and an analytical measurement test sample group identification number of the same first identification numbers.

Moreover, it is preferred that the pieces of the analytical measurement test item information are grouped so as to include at least one of an analytical measurement test item corresponding to the analytical measurement test sample group identification number of the first identification numbers and the designation of an output format having a lower limit value, an analysis accuracy and an analytical measurement test value of the analytical measurement test regarding the analytical measurement test method corresponding to the analytical measurement test item, and the grouped units of the information are stored in the storage means, whereby the information can be promptly and efficiently processed and the extremely reliable test results can be reported.

Furthermore, it is preferred that the above-mentioned relevant information comprises the analytical measurement test method information of the pieces of the first group information including at least analytical measurement test method names, and the analytical measurement test information of the pieces of the first group information includes information regarding the unit of the analytical measurement test value corresponding to the analytical measurement test item.

It is preferred that the analytical measurement test method information comprises at least one of an analytical measurement test unit price corresponding to the analytical measurement test method recognized by the analytical measurement test method name to which the identification number is given, and analytical measurement test unit prices corresponding to a plurality of analytical measurement test methods recognized by the analytical measurement test method group name to which the identification number is given.

It is preferred that final results to be sent to a customer include at least a customer name, an analytical measurement test sample name, an analytical measurement test item, an analytical measurement test value and a unit of the analytical measurement test value, and they are then output in a uniform format, whereby the results can easily be controlled by the customer. Moreover, it is preferred that the analytical measurement test value in the final results is rounded off by at least one of pieces of information regarding a lower limit value, an analysis accuracy and an output format designation of the analytical measurement test method corresponding to the analytical measurement test item, whereby the reliability of the analytical measurement test value can be improved.

It is desirable that the final results include information regarding a cost of the analytical measurement test taken to obtain the final results, and it is also desirable that at least one of an error range, a reliability limit and an analysis accuracy is written as an analytical measurement test value, whereby the reliability of the test values can be improved.

The present invention will be described in more detail with reference to embodiments. However, the scope of the present invention should not limited to these embodiments.

Embodiment 1

Embodiment 1 of the present invention will be described below by taking a case of executing a chemical analysis test of a raw material for quality control of the raw material such as an acceptance test of a raw material in the manufacturing department as an example.

As shown in FIG. 1, the automatic analysis system of this embodiment is constituted by connecting analytical measurement test equipments such as analytical equipment 1a, analytical equipment 1b and analytical equipment 1c having control computers 2a, 2b and 2c, respectively, with a computer 3 exclusively used for a data base system, a work station 4 serving as an input/output terminal, and a laser beam printer 5 by a network such as Ethernet or FDDI (Fiber Distributed Data Interface). The analytical measurement test equipments and the computer used for the data base system are set in the chemical analysis department.

Unless the manufacturing department is located with the chemical analysis department in the same site, it is preferable to connect terminals 4 and 5 of the manufacturing department with the host computer 3 exclusively used for the data base system by WAN (Wide Area Network) or a public data network.

In the case of this embodiment, the host computer 3 is set in the chemical analysis department. However, it is needless to say that the computer 3 can be set anywhere as long as it is connected to a network.

FIGS. 3 to 11 show the outline of the processing sequence according to the automatic analysis system of this embodiment. The host computer 3 has a built-in data base system provided with storage means and control means. The storage means of the data base system previously stores customer names, analytical measurement tester names, analytical measurement test sample group names, analytical measurement test item names, analytical measurement test method names, and unit names together with first identification numbers of integers, real numbers, or negative numbers in order to identify and relate the above-mentioned names, to read out them at a high speed, and to simplify the handling of information in the computer.

The above-mentioned first identification numbers for identifying information are automatically numbered by the control means of the host computer 3 so that they are not overlapped. Moreover, the storage means previously stores analytical measurement test conditions, and the lower limit value of the analytical measurement test, accuracy of the analytical measurement test, and analytical measurement test value rounding-off method by making them correspond to analytical measurement test sample groups, analytical measurement test items, and analytical measurement test methods. The analytical measurement test value rounding-off method conforms to JIS Z8401 (Rules for Rounding Off of Numerical Values).

The information to be previously stored including customer names, analytical measurement tester names, analytical measurement test sample group names, analytical measurement test item names, analytical measurement test method names, unit names, analytical measurement test conditions, and the lower limit value of analytical measurement test and analytical measurement test value rounding-off method is basic information for systematically operating the data base system of this embodiment and also referred to as master information. It is necessary to store a new customer or a new analytical measurement test sample group whenever it appears. To process one's belonging section, a FAX number, and a telephone number of a customer and the cost for an analytical measurement test, it is preferable to store the customer's bank account number and his shouldered code as master information.

An analytical measurement test sample group in this embodiment is first group information obtained by considering the property, chemical composition, and analytical measurement test method of analytical measurement test samples and thereby grouping the analytical measurement test samples and its name is shown by approx. three alphabetical characters because the name can easily be handled. For example, when an analytical measurement test sample is made of quartz, quartz sand, or silica rock brick, the name of the analytical measurement test sample group uses, for example, "QRZ" associating Quartz. Similarly, it is convenient to use approx. three alphabetical characters capable of associating an analytical measurement test method as an analytical measurement test name.

The processing of an analytical measurement test sample is set so that, when an analytical measurement test sample group is determined, a normal analytical measurement test item is determined, an analytical measurement test method is determined correspondingly to the analytical measurement test item, and a analytical measurement test value rounding-off method is determined.

The input/output terminal of this embodiment is set in both chemical analysis department and manufacturing department. Thereby, when a chemical analysis test is completed in the chemical analysis department, chemical analysis test results can immediately be accessed from the manufacturing department. Therefore, the chemical analysis test results can quickly be used for the quality control of a raw material such as decision on acceptance or not of the raw material.

Figure 2:
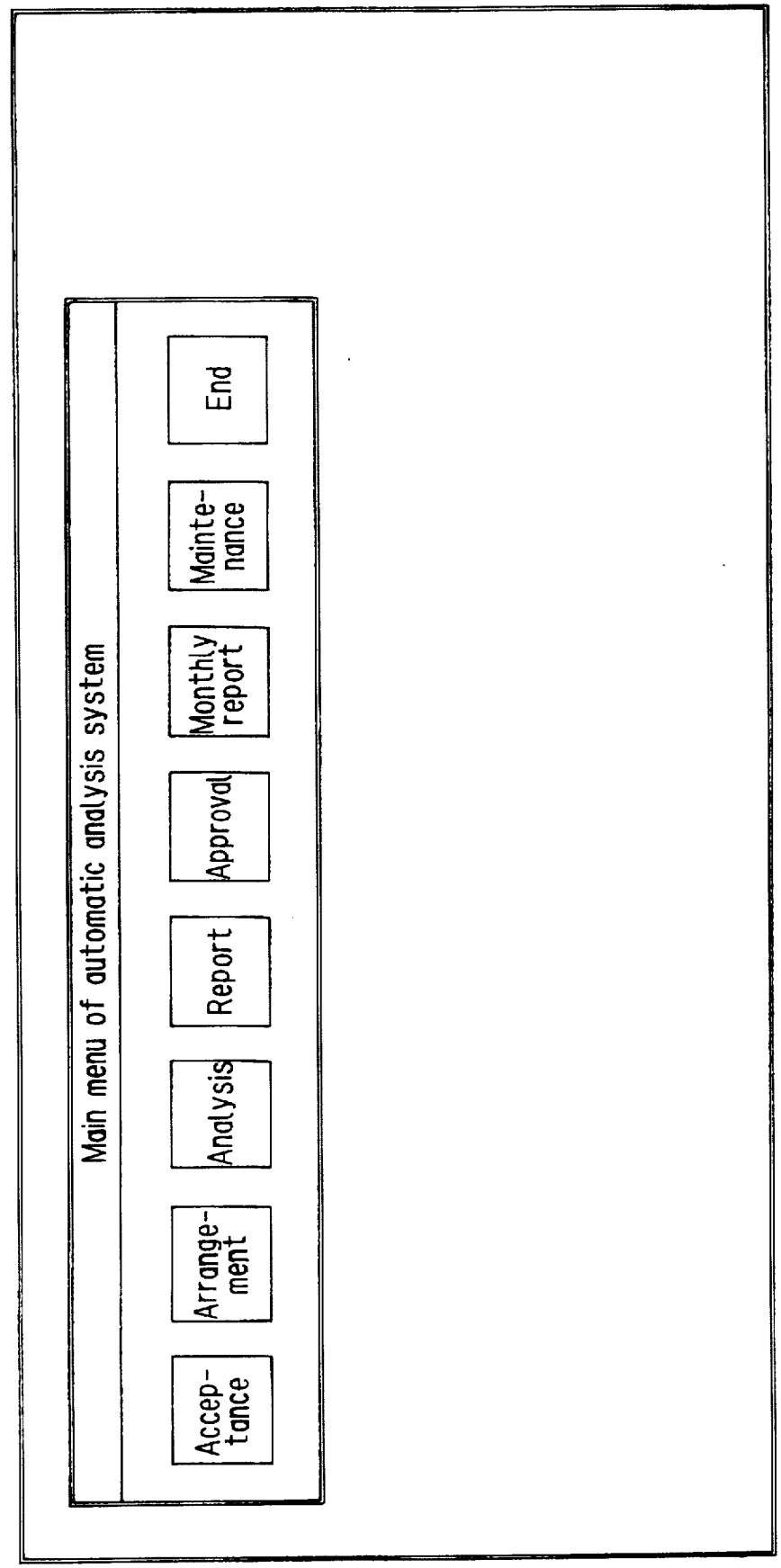
FIG. 2 is an example of a main menu.

FIG. 2 shows a main menu and FIGS. 3 to 11 are flow charts showing an example of this system.

Figure 3:
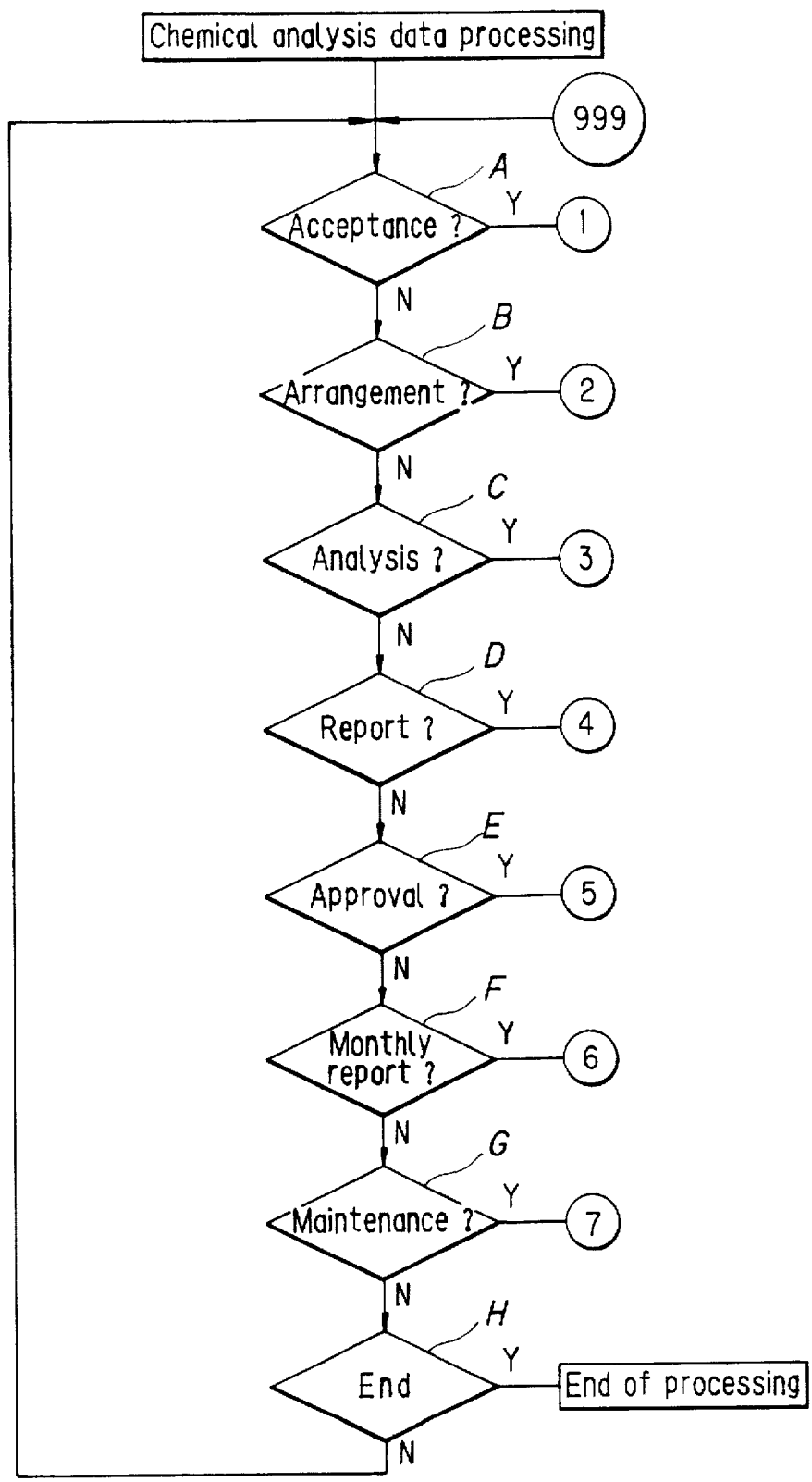
FIG. 3 is a whole flow chart showing the sequence of chemical analysis data processing which is an embodiment of the present invention.

FIG. 3 shows a flow chart of the whole sequence of chemical analysis data processing. In the case of routine operation, data processing is generally performed in the sequence of "acceptance"A→"arrangement"B→"analysis"C→"report"D→"approval"E→"end" F. FIGS. 4 to 9 show each specific processing procedure.

Next, detailed description will be made.

When a chemical analysis test of a raw material is necessary, necessary matters such as a requester's name corresponding to a customer name, an analytical measurement test sample name, and an analytical measurement test item name are entered in a chemical analysis request form shown in FIG. 12 provided with a request number for identifying the chemical analysis request form and sent to the chemical analysis department together with an analytical measurement test sample. The number of analytical measurement test samples may be 1, 5, or 20 for one chemical analysis form. The number of analytical measurement test samples is not limited.

When the analytical measurement test sample is sent from the manufacturing department to the chemical analysis department together with the chemical analysis request form, a person in charge in the chemical analysis department performs the "acceptance" processing of the analytical measurement test sample for inputting the customer information which belongs to the first group information including the request form number, requester's name, and requester's belonging section and sample information which belongs to the first group information including the analytical measurement test sample name from a terminal in accordance with the entries in the chemical analysis request form.

Figure 4:
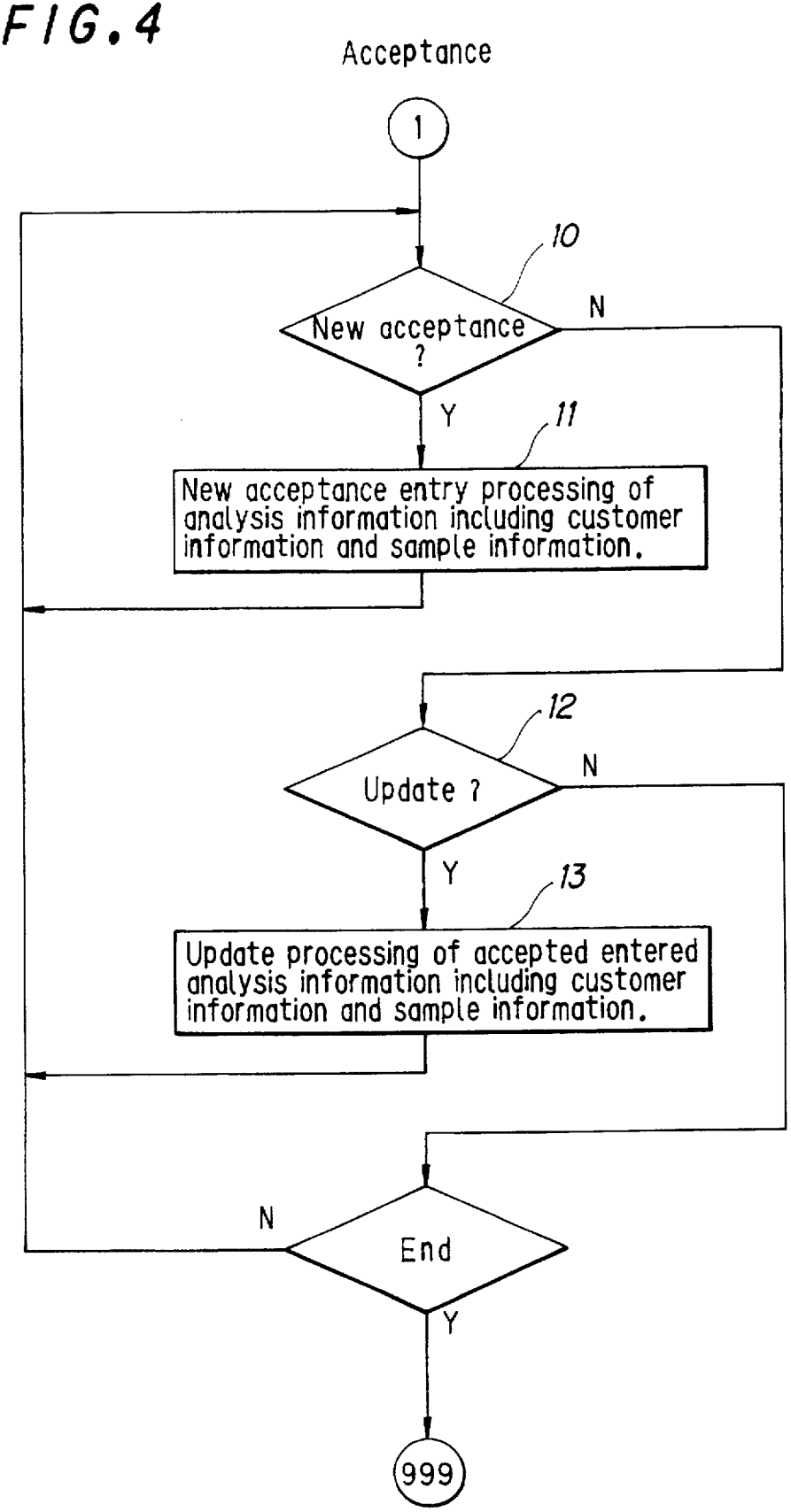
FIG. 4 is a flow chart showing the sequence of "acceptance" processing.

The "acceptance" processing executed with the input terminal (input means) 4 of a work station or the like will be described in more detail with reference to FIGS. 2, 4, and 20.

In the case of the main menu shown in FIG. 2, "acceptance" is clicked with a mouse to open the screen of "acceptance". The request form number input field is clicked with the mouse to input the request number of the chemical analysis request form (steps 10 and 11). When a request form number already stored in the storage means of the data base system is input at this point of time, the information related to the request form number is read out of the storage means of the data base every acceptance information which belongs to the second group information grouped by relating customer information, analytical measurement test sample information, measured data information, analytical measurement test item name information, analytical measurement test method information and analytical measurement test sample group information which belong to the first group information to a customer identification number, an analytical measurement test sample identification number, an analytical measurement test sample group identification number, an analytical measurement test item identification number, and an analytical measurement test method identification number of the first identification numbers, respectively, displayed on a screen, and update processing for changing the above-mentioned pieces of information and storing them again is executed (steps 12 and 13).

Similarly, by moving the mouse cursor to the requester's belonging section input field, a selective window displaying prospective requester's belonging section names opens. When a purposed customer's belonging section name is clicked with the mouse, the requester's belonging section name is input. One's belonging section name is converted into a first identification number of an integer, a real number or a negative number for identifying the name and stored in the storage means of the data base system. Then, the mouse cursor is moved to the requester's name input field. Because a selective window displaying prospective requesters related to their belonging sections opens, a purposed requester's name is input by clicking it with the mouse. The requester's name is converted into a first identification number of an integer, a real number or a negative number for identifying the name and stored in the storage means of the data base system. When processing of the cost for the analytical measurement test is necessary, it is necessary to input the customer's bank account number or his shouldered cost code in accordance with manipulations similar to those already described.

Figure 21:
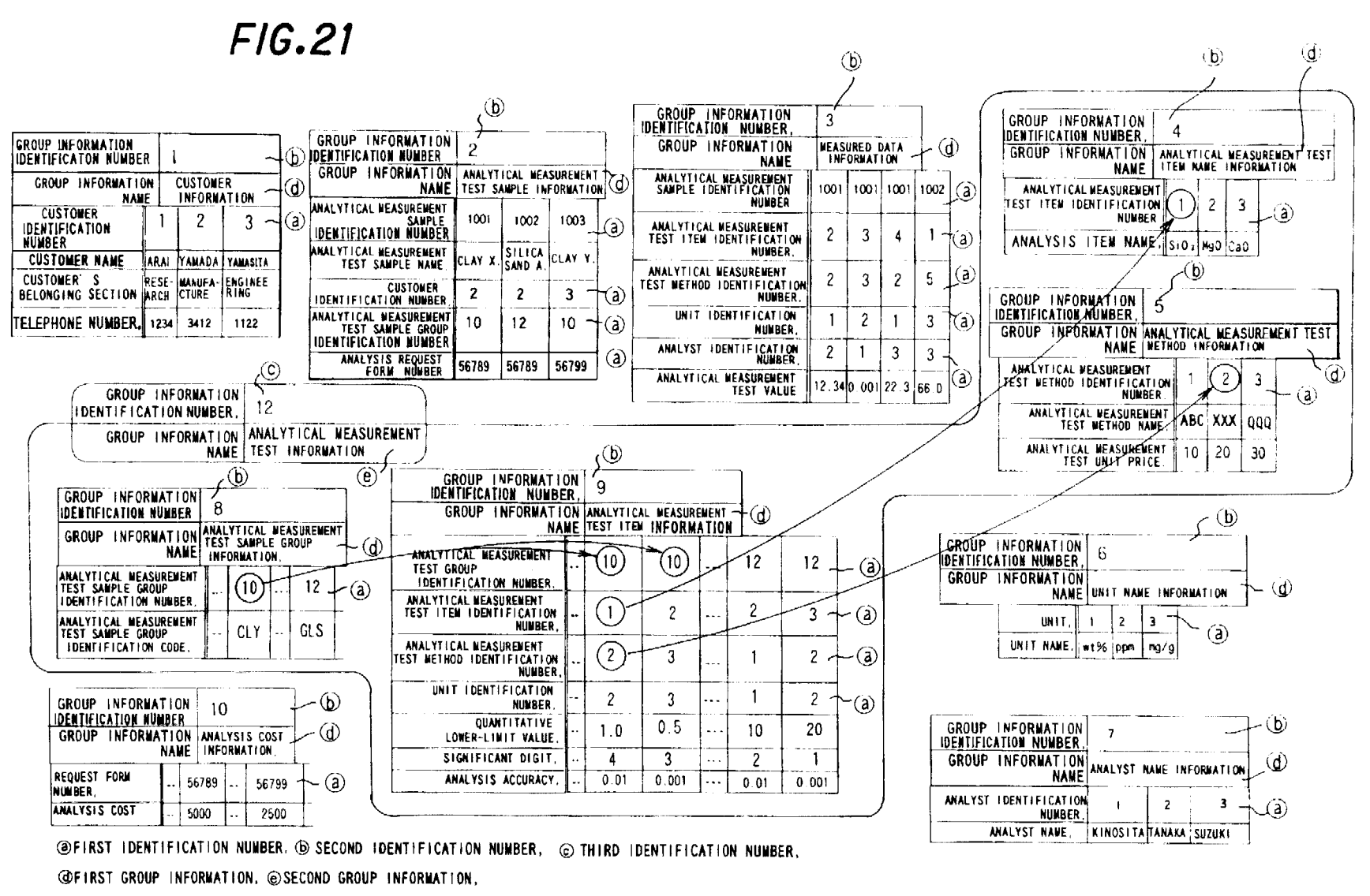

Then, the analytical measurement test sample name entered in the chemical analysis request form is input. Then, the analytical measurement test sample group name related to the analytical measurement test sample is input. The purposed analytical measurement test sample group name is can also be input by clicking it because a selective window displaying prospective analytical measurement test sample group names opens by moving the mouse cursor to the analytical measurement test sample group name input field. When the analytical measurement test sample group name is input, the present automatic analysis system automatically displays an analytical measurement test item necessary for the analytical measurement test sample and an analytical measurement test method corresponding to the analytical measurement test item. In this case, pieces of information such as an analytical measurement test item and an analytical measurement test method corresponding to the analytical measurement test item are, as shown in FIG. 21 by an arrow, read out of the storage means of the data base every analytical measurement test information which belongs to the second group information grouped by relating analytical measurement test sample group information, analytical measurement test item information, analytical measurement test item name information, and analytical measurement test method information which belong to the first group information to an analytical measurement test sample group identification number, an analytical measurement test item identification number, and an analytical measurement test method identification number, respectively. When the number of analytical measurement test items is excessive or insufficient, new analytical measurement test item names and analytical measurement test method names are added or displayed analytical measurement test items are deleted. In this case, it is more preferable to input an analyst name in charge of the analytical measurement test correspondingly to analytical measurement test items. An analytical measurement test item name, analytical measurement test method name, and analyst name are converted into identification numbers of integers, real numbers, or negative numbers for identifying the names and stored in the storage means of the data base system.

Then, an analysis due date is input. The priority of analysis is automatically determined and input by the control means of the computer 3 in accordance with the input analysis due date. Moreover, if necessary, a comment corresponding to an analytical measurement test sample is input. The comment input here is special mention on the analytical measurement test sample of an analytical measurement test method, which is entered in an arrangement form to be mentioned later and referenced and effectively used when an analytical measurement test is executed. Finally, input information is confirmed through a screen and thereafter, entry in the data base system is designated to terminate the "acceptance" processing. The information input sequence is described so that a terminal is smoothly manipulated, but it is a matter of course that the sequence is not restricted to the case of this embodiment.

Figure 5:
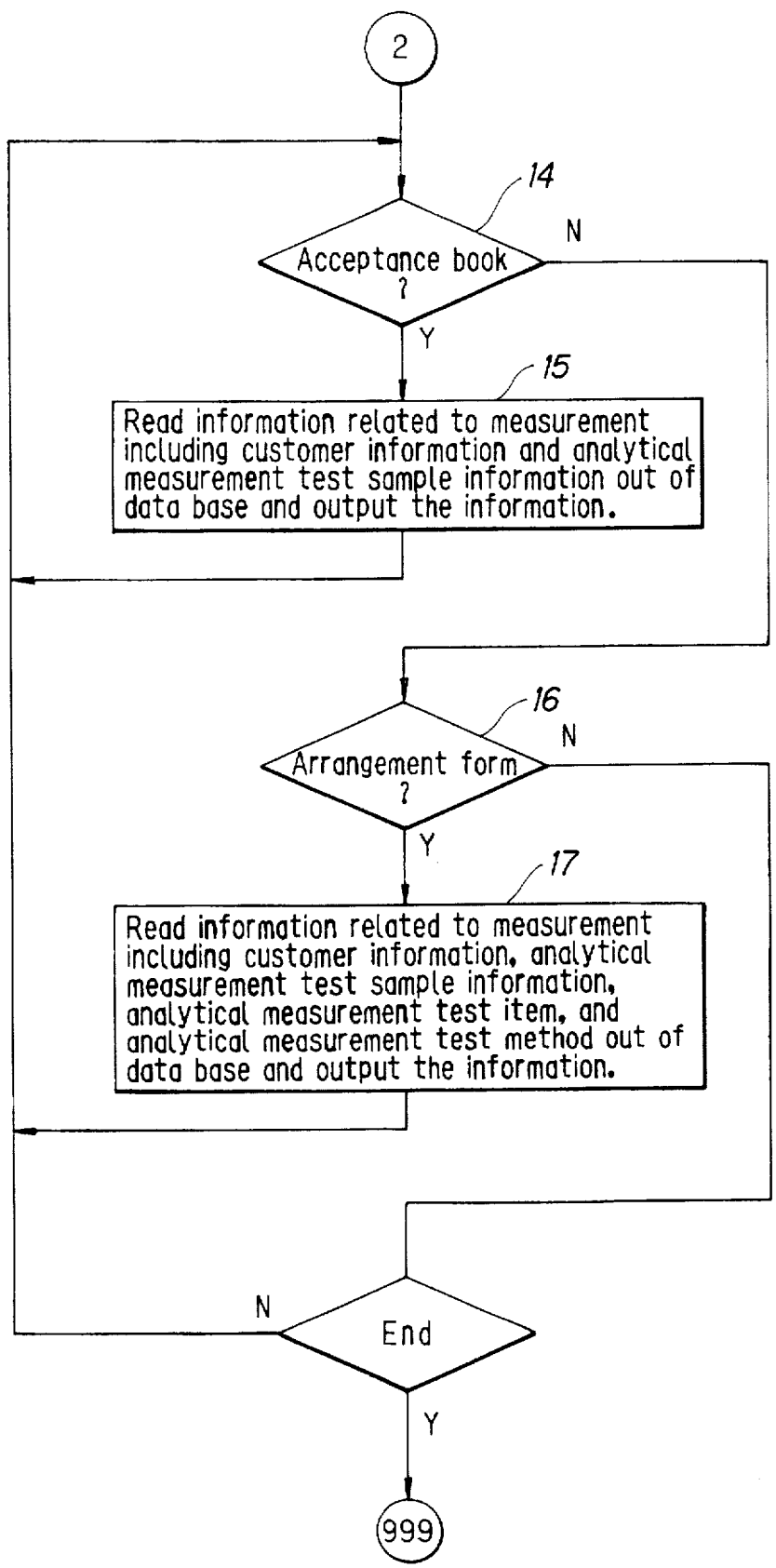
FIG. 5 is a flow chart showing the sequence of "arrangement" processing.

Before a chemical analysis test is executed, the arrangement form shown in FIG. 13, for example, is output in accordance with the sequence of steps 14 to 17 in FIG. 5. In this case, customer information, analytical measurement test sample information, measured data information, analytical measurement test item name information, and analytical measurement test method information which belong to the first group information necessary for outputting the arrangement form are read out of the storage means of the data base every arrangement form information which belongs to the second group information grouped by relating the above-mentioned pieces of information to a customer identification number, an analytical measurement test ample identification number, an analytical measurement test item identification number and an analytical measurement test method identification number, respectively.

The arrangement form supplies the respective pieces of analysis information necessary for a chemical analysis test to an analyst through an instruction form allowing the analyst to correctly and smoothly execute the chemical analysis test before the chemical analysis test is executed by preparing the respective pieces of analysis information such as an analytical measurement test item on which the chemical analysis test is executed, and an analytical measurement test sequence, analytical measurement test method, analytical measurement test condition necessary to execute the chemical analysis test and storing them in a memory by control means, reading them out of the memory for each desired viewpoint such as an analytical measurement test method or a group in charge of analytical measurement test, and outputting their data to output means such as a printer.

Specifically, the respective pieces of analysis information necessary for a chemical analysis test such as analytical measurement test items of an analytical measurement test sample, an analytical measurement test method for each analytical measurement test item, analytical measurement test conditions, an analyst name, a group in charge of analytical measurement test related to the chemical analysis test of the analytical measurement test sample, an analysis due date, and instructions of a responsible person in the chemical analysis department related to the chemical analysis test of the analytical measurement test sample are entered in the arrangement form in the best analytical measurement test sequence on, for example, a chemical composition, analysis due date, criticality, and time necessary for the chemical analysis test by considering the efficiency and accuracy of the chemical analysis test, and data can be output for each desired viewpoint such as an analytical measurement test method or group in charge of analytical measurement test. Therefore, the following advantages can be obtained by executing the chemical analysis test in accordance with the details entered in the arrangement form.

(1) A high-accuracy chemical analysis test can be executed.

Because the respective pieces of analysis information are entered in an arrangement form in the sequence of analytical measurement test samples considering the chemical compositions of analytical measurement test items of the analytical measurement test samples, a high-accuracy chemical analysis test can be executed, that is to say, for example, it is possible to minimize the influence of the difference of chemical composition between analytical measurement test samples on measured data such as contamination between analytical measurement test samples by executing a chemical analysis test in the sequence of the analytical measurement test samples entered in the arrangement form.

For example, a case will be described below in which a crushing-mixing operation of an analytical measurement test sample which is a pretreatment operation of the analytical measurement test sample is executed in one crushing-mixing vessel successively in accordance with the fluorescent X-ray analysis method which is one of the chemical analysis test methods. An automatic analysis system of the present application makes it possible to enter analytical measurement test samples in an arrangement form starting with an analytical measurement test sample with the lowest content of $SiO_2$ when analyzing $SiO_2$ as an analytical measurement test item. Therefore, by executing a chemical analysis test in the sequence of the analytical measurement test samples entered in the arrangement form, a high-accuracy chemical analysis test can be executed, that is to say, for example, the contamination between analytical measurement test samples through the crushing-mixing vessel is minimized.

To apply the crushing-mixing operation to a plurality of analytical measurement test samples with different matrix components or different chemical compositions in one crushing-mixing vessel successively as described above, the crushing-mixing operation is normally executed by using analytical measurement test samples to which the crushing-mixing operation is applied in the subsequent sequence in order to clean the crushing-mixing vessel for preventing the contamination between analytical measurement test samples and samples with similar matrix components or chemical compositions, that is to say, the so-called sacrificed samples and thereafter, the crushing-mixing operation is applied to the analytical measurement test sample in the subsequent sequence between crushing-mixing operations of analytical measurement test samples with different matrix components or chemical compositions in order to prevent the matrix components or chemical compositions of the analytical measurement test samples to which the crushing-mixing operation is applied in the precedent sequence from influencing measured data for analytical measurement test items of the analytical measurement test samples to which the crushing-mixing operation is applied in the precedent sequence.

The automatic analysis system of the present application makes it possible to group analytical measurement test samples with similar matrix components or analytical measurement test samples with similar chemical compositions by the matrix components or chemical compositions of the analytical measurement test samples and enter groups of analytical measurement test samples in an arrangement form every group of them. As described above, it is unnecessary to execute the crushing-mixing operation for preventing the matrix components or chemical compositions of the analytical measurement test samples to which the crushing-mixing operation is applied in the precedent sequence from influencing the measured data for analytical measurement test items of the analytical measurement test samples to which the crushing-mixing operation is applied in the subsequent sequence through the crushing-mixing vessel between crushing-mixing operations of the analytical measurement test samples with similar matrix component or similar chemical compositions.

Therefore, by executing a chemical analysis test in the sequence of the analytical measurement test samples entered in the arrangement form, it is possible to continuously apply the crushing-mixing operation to analytical measurement test samples with similar matrix components or similar chemical compositions. Thus, the number of crushing-mixing operations of the samples is minimized, the frequency of crushing-mixing operations for sacrificed samples is also minimized, and high-efficiency high-accuracy chemical analysis test can be executed.

(2) An efficient chemical analysis test can be executed.

The respective pieces of analysis information can be entered in an arrangement form in the analytical measurement test sequence considering analytical measurement test conditions such as an analytical measurement test time and an analysis temperature of an analytical measurement test sample. Therefore, by executing an analytical measurement test in the sequence of the analytical measurement test samples entered in the arrangement form, it is possible to execute a chemical analysis test because analytical measurement test systems can always efficiently be operated and analytical measurement test instruments can always efficiently be arranged.

For example, an operation for vitrifying an analytical measurement test sample will be described below in which an analytical measurement test sample vitrifying system is used which is one of the analytical measurement test sample pretreatment systems according to the fluorescent X-ray analysis method. Some of the systems can vitrify a plurality of analytical measurement test samples at the same time when the samples have the same vitrifying condition which is one of the analytical measurement test conditions. As described above, analytical measurement test samples are entered in the arrangement form in the listed sequence of analytical measurement test samples with the same treatment condition by considering analytical measurement test conditions such as an analytical measurement test time and an analysis temperature so that the operation efficiency of the system is optimized. Therefore, an efficient operation can be performed by vitrifying analytical measurement test samples in the sequence of the analytical measurement test samples entered in the arrangement format.

(3) It is possible to accurately, flexibly, and quickly take actions for a schedule change of a chemical analysis test.

Because the respective pieces of analysis information can entered in an arrangement form for each desired viewpoint such as an analyst or an analytical measurement test method, it is possible to accurately, flexibly, and quickly take necessary actions for a schedule change of a chemical analysis test by referring to the arrangement form.

For example, when urgent actions must be taken because a chemical analysis test cannot quickly be executed due to absence of an analyst, it is possible that another analyst can easily execute the chemical analysis test by using the analytical measurement test sample entered in the arrangement form of the absent analyst in accordance with the analytical measurement test conditions also entered in his arrangement form, that is to say, only by reading the arrangement form of the absent analyst. Therefore, it is possible to take actions flexibly and quickly.

(4) Analysis arrangement can always be made at the highest operation efficiency.

For example, when an initially scheduled chemical analysis test cannot be completed because an unexpected urgent chemical analysis test is executed, it is possible to output an arrangement form in which analytical measurement test samples are entered in the analytical measurement test sequence considering all analytical measurement test samples including the analytical measurement test sample whose chemical analysis test could not be completed and the newly-accepted analytical measurement test sample so that the highest operation efficiency and accuracy can be obtained as described above when outputting the arrangement form on the following day. Therefore, by executing analysis arrangement in accordance with the respective pieces of analysis information entered in the arrangement form, analysis arrangement can always be made at the highest chemical analysis test operation efficiency.

(5) It is possible to flexibly take actions for exceptions.

For example, when an analytical measurement test must urgently be executed, it is possible to output an arrangement form in the analytical measurement test sequence having priority to an urgent analytical measurement test sample by the fact that analyst having a privilege of a certain level or higher such as a chemical analysis room responsible person inputs an instruction representing an urgent action for the analytical measurement test sample information of the urgent analytical measurement test sample. Therefore, it is possible to flexibly take actions for exceptions and perform an analytical measurement test by executing a chemical analysis test in the sequence of the analytical measurement test samples entered in the arrangement form.

(6) The number of artificial errors in an analytical measurement test can be minimized.

For example, because a list of pieces of information necessary to execute an analytical measurement test such as a necessary number of analytical measurement test samples according to the fluorescent X-ray analysis method is entered in an arrangement form, the number of artificial errors such as execution of a chemical analysis test under an incorrect analysis condition is minimized by executing an analytical measurement test in accordance with the details entered in the arrangement form.

The arrangement form in FIG. 13 will be described in more detail.

This arrangement form is an arrangement form for measurement of loss on ignition which is one of the analytical measurement test items, in which a request form number to execute the loss-on-ignition measurement on an arrangement-form output date, analytical measurement test sample name, analysis due date, ignition temperature, and type of crucible to be used are entered. Any analyst can accurately and smoothly execute the loss-on-ignition measurement in accordance with the arrangement form. Therefore, the number of simple errors such as confusion of an ignition temperature and the type of crucible to be used which have occurred so far is decreased to zero by applying the present system.

Figure 6:
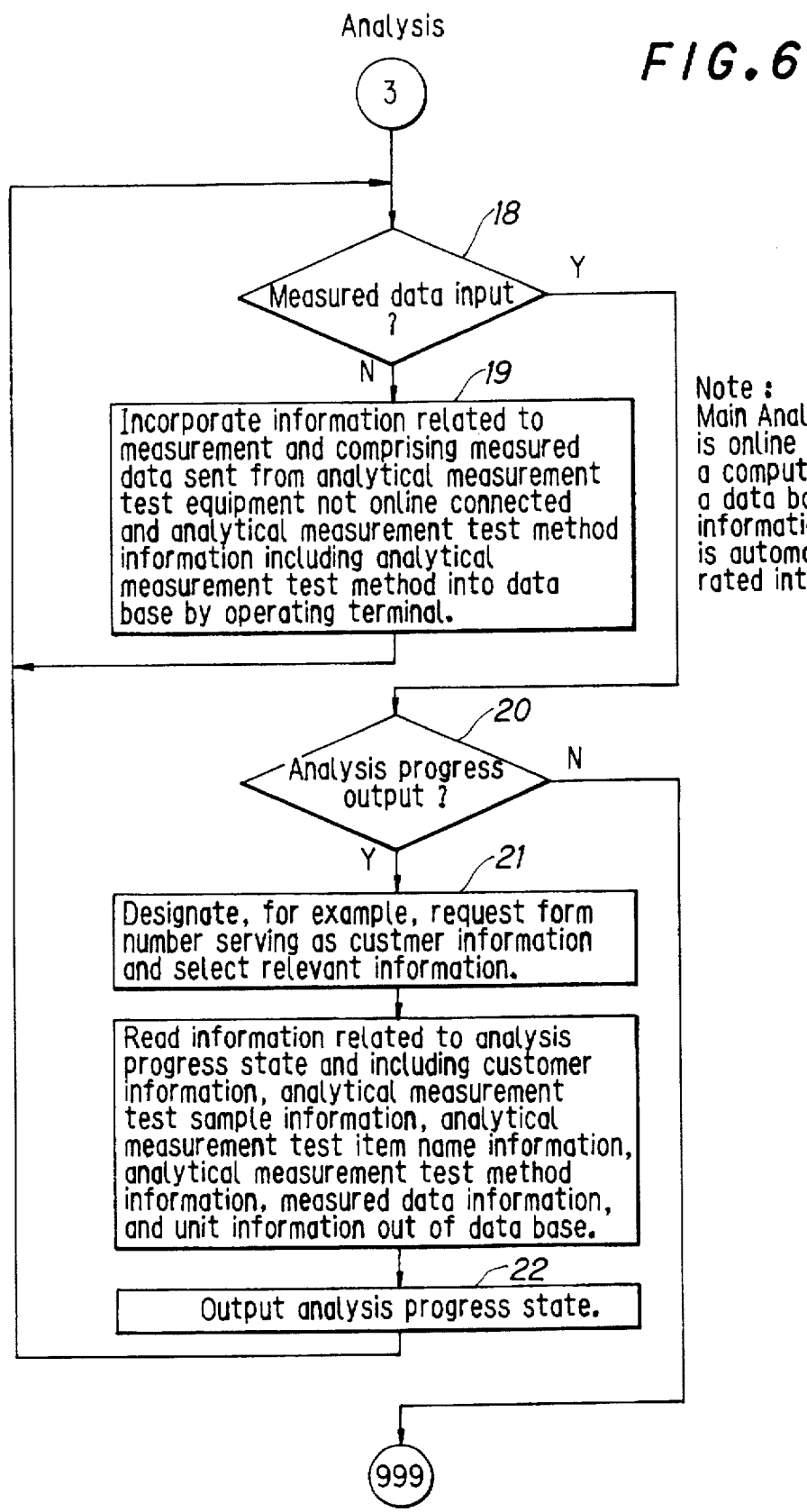
FIG. 6 is a flow chart showing the sequence of "analysis" processing.
Figure 7:
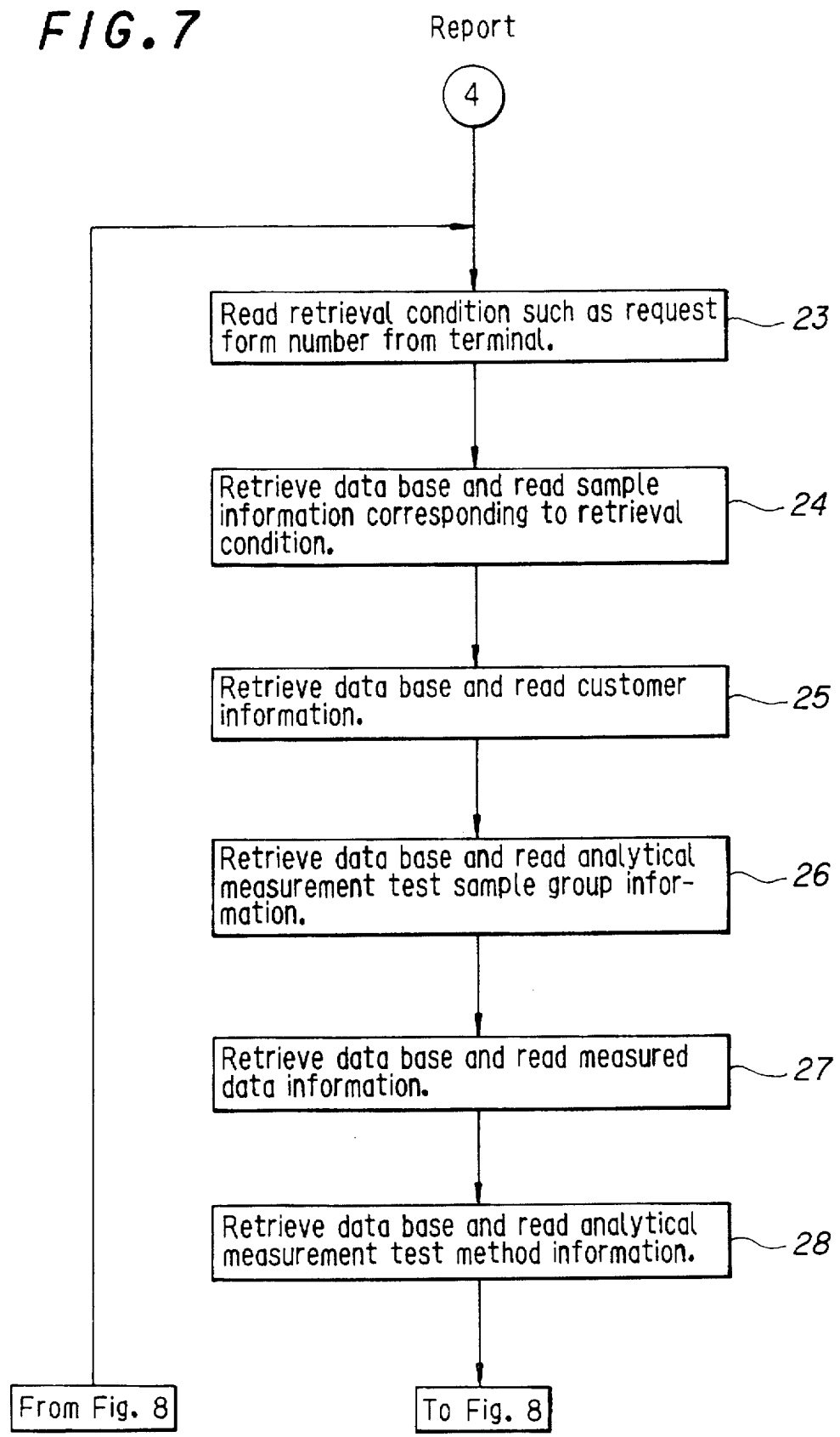
FIG. 7 is a flow chart showing the sequence of "report" processing.
Figure 8:
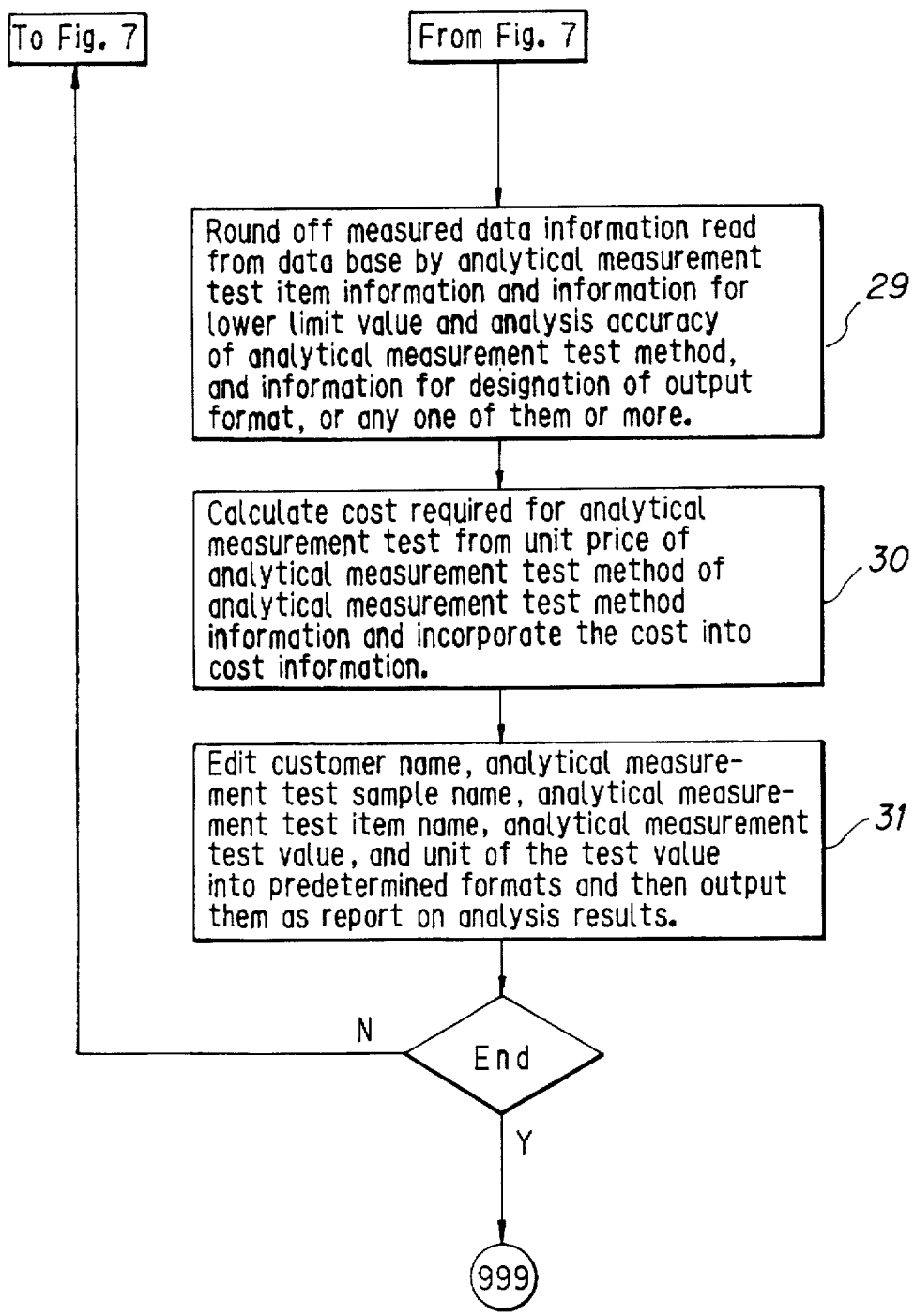
FIG. 8 is a flow chart showing the sequence of "report" processing.

Then, the "analysis" processing is executed in accordance with the sequence of steps 18 and 19 in FIG. 6. In this case, to execute a chemical analysis test, one analytical measurement test sample may have one analytical measurement test item or a plurality of analytical measurement test items. Moreover, it may be possible to execute an analytical measurement test for a plurality of analytical measurement test items by one type of analytical measurement test equipment and one type of analytical measurement test method or analytical measurement test equipment and an analytical measurement test method to be used may change for each analytical measurement test item. Furthermore, the same analytical measurement test equipment and same analytical measurement test method may be used for an analytical measurement test of the same type of analytical measurement test items a plurality of times. Furthermore, an analyst who executes a chemical analysis test may change depending on an analytical measurement test item, analytical measurement test equipment, or analytical measurement test method. The item, equipment, or method is determined by considering the efficiency and accuracy of an analytical measurement test in many cases.

An analyst executes a chemical analysis test in accordance with an arrangement form. Analytical measurement test equipments 1a, 1b, and 1c are connected with the host computer 3 exclusively used for the data base system through attached control computers 2a, 2b, and 2c. Therefore, when a chemical analysis test is completed, measured data is on-line transferred to the storage means of the data base of the host computer 3 and stored in the data base. When there is an analytical measurement test equipment or it is necessary to input measured data according to an analytical measurement test method in the host computer 3, it is possible to manually input the data from a terminal by manipulating a mouse.

After the measured data is stored in the storage means of the data base, it is on-line transferred and then, the stored measured data and the measured data manually input by manipulation of a mouse are handled in the completely same manner. The storage means of the data base system stores the history of these measured data in detail. Therefore, when measured data is claimed by a customer or requester, it is possible to immediately correspond to the claim of the customer or requester and provide high-reliability chemical analysis test results.

In the case of a chemical analysis test, a plurality of analytical measurement test samples are tested by a plurality of analysts in many cases depending on an analytical measurement test item. This is because it is possible to quickly provide chemical analysis test results. In this case, a situation in which the progress state of a chemical analysis test must be studied frequently occurs in order to progress the chemical analysis test more quickly, accurately, and smoothly, keep the delivery due date of a customer, and evaluate the validity of the chemical analysis test results.

The present system can easily realize the above mentioned. That is to say, as shown in steps 20 to 22 in FIG. 6, "analysis" is clicked with a mouse, for example, a request form number is designated, and "analysis progress" is clicked (steps 20 and 21). Instantaneously, the progress state of a chemical analysis test related to a chemical analysis request form designated by the request form number is displayed on the screen (step 22).

Figure 23:
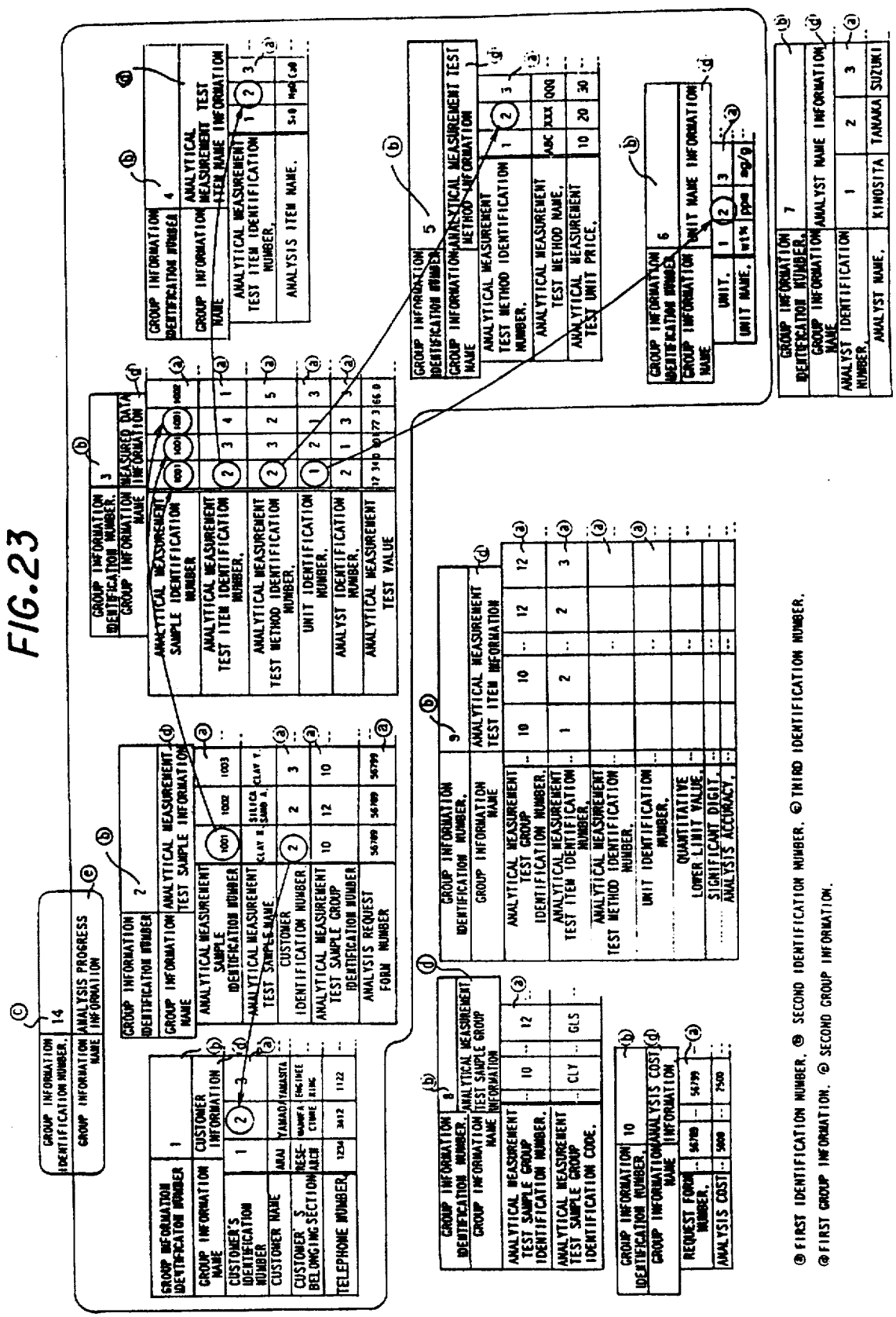
FIG. 23 shows "analysis progress information" as one example of relating and grouping the respective pieces of analysis information.

In this case, analytical measurement test sample information, measured data information, analytical measurement test item name information, analytical measurement test method information, and unit name information which belong to the first group information necessary to display the analysis progress state are read out of the storage means of the data base every analysis progress information which belongs to the second group information grouped by relating the above-mentioned pieces of information to a customer identification number, an analytical measurement test sample identification number, an analytical measurement test item identification number, an analytical measurement test method identification number and a unit identification number of the first identification numbers, respectively, as shown by arrows in FIG. 23.

In the case of analysis progress, it is possible to inquire the information for the analysis progress state of an analytical measurement test sample or the like at that point of time in detail. For example, it is possible to immediately and accurately inquire the latest information about a request form and analytical measurement test sample, measured data for each analytical measurement test item, final results, analyst, analytical measurement test method, views of responsible person in the chemical analysis department or analyst, and relevant analytical measurement test group. Thereby, for example, the following advantages are obtained.

(1) A chemical analysis test can accurately and quickly be controlled.

For example, it is possible to enter and output a list of analytical measurement test samples whose analysis due date expires together with an analytical measurement test method and an analyst name. Thereby, an analytical measurement test sample whose delivery due date expires is clarified and actions can be taken quickly and accurately.

(2) The efficiency of a chemical analysis test is improved.

For example, it is possible to inquire the latest information related to the analysis progress such as completion or not of a chemical analysis test, an analyst in charge of the chemical analysis test of each analytical measurement test item, and an analytical measurement test method on analytical measurement test items of a designated analytical measurement test sample. Therefore, it is possible to accurately and smoothly perform the communication between a responsible person and an analyst and between analysts in the chemical analysis department. Thus, when a particular analytical measurement test is delayed, it is possible to flexibly take actions for adjustment of the progress of a chemical analysis test such as arrangement of analytical measurement test equipment or an analyst and resultingly, the efficiency of the chemical analysis test is improved.

(3) Services for customers are improved.

For example, it is possible to inquire the information related to analysis progress such as completion or incompletion of a chemical analysis test of an analytical measurement test item of a designated analytical measurement test sample for each analytical measurement test method. Therefore, it is possible to immediately and accurately respond to an inquiry about the halfway progress of a chemical analysis test or the scheduled completion date of the test and services for customers are improved.

When chemical analysis tests of all analytical measurement test items are completed, a report on chemical analysis test results is immediately prepared. In the case of the present system, a report on chemical analysis test results is automatically prepared in accordance with steps 23 to 31 in FIGS. 7 and 8 and protected as described later. That is to say, when a retrieval condition such as a requester number is input from a terminal (input means) (step 23), the control means of the present data base system reads analytical measurement test sample information, customer information, analytical measurement test sample group information, measured data information, and analytical measurement test method information which correspond to the retrieval condition and are the first group information by relating these pieces of the information to each other (steps 24 to 28). A second identification number is given to the first group information to distinguish between the groups. In this case, a customer identification number which belongs to the first identification number of the analytical measurement test sample information is related to a customer identification number which belongs to the first identification number of the customer information and a third identification number showing the relation between the customer identification numbers is given. Similarly, an analytical measurement test sample group identification number which belong to the first identification number of the analytical measurement test sample information is related to an analytical measurement test sample group identification number which belongs to the first identification number of the analytical measurement test sample group information and a third identification number showing the relation is given. Moreover, an analytical measurement test sample identification number which belongs to the first identification number of the sample information is related to an analytical measurement test sample identification number which belongs to the first identification number of the measured data information and a third identification number showing the relation is given. Furthermore, an analytical measurement test method identification number which belongs to the first identification number of the analytical measurement test sample group information is related to an analytical measurement test method identification number which belongs to the first identification number of the analytical measurement test method information and a third identification number showing the relation is given.

Any analyst can prepare a report of chemical analysis test results as long as the analyst is registered in the present system, though the analyst qualification is checked by a password. In the case of this embodiment, an analyst finally executing a chemical analysis test of an analytical measurement test item or an analyst finally obtaining measured data designates preparation for a report on chemical analysis test results to the host computer from a terminal. Specifically, by clicking "report" in the main menu with a mouse, then designating, for example, a request form number, and clicking "normal report", a screen for editing a report on chemical analysis test results is displayed. In this case, analytical measurement test sample information, customer information, analytical measurement test sample group information, measured data information, analytical measurement test item name information, analytical measurement test method information, unit name information, and analysis cost information which belong to the first group information necessary for preparing a report on chemical analysis test results are read out of the storage means of the data base every analysis result report information which belongs to the second group information grouped by relating the above pieces of information to a customer identification number, an analytical measurement test identification number, an analytical measurement test sample group identification number, an analysis request form number, an analytical measurement test item identification number, an analytical measurement test method identification number and a unit identification number, respectively. In the case of normal operation, an initial value displayed on each input field can be used but it is unnecessary to change it when the above screen is displayed. However, it is necessary to input a special processing such as a case of entering a comment in a report on chemical analysis test results to the above screen. Then, it is designated to finally prepare a report on chemical analysis test results. For example, the report on chemical analysis test results shown in FIG. 14 is prepared (step 31).

To prepare a report on chemical analysis test results, a chemical analysis test value is automatically rounded off depending on an analytical measurement test item, analytical measurement test method, rounding-off method, and the lower limit value of an analytical measurement test (step 29). Moreover, the chemical analysis test value is put down together with a 95% confidence limit value according to necessity. Furthermore, a cost required for the chemical analysis test is calculated in accordance with step 30 and incorporated into analysis cost information. In this case, a request form number which belongs to the first identification number of the analytical measurement test sample information and a request form number which belongs to the first identification number of the analysis cost information are related to each other and incorporated into the analysis cost information.

The following advantages are obtained from the chemical analysis test result report preparing function of the present automatic analysis system.

(1) A report on chemical analysis test results can be prepared accurately and quickly.

To prepare a report on chemical analysis test results, usually, the information necessary for preparing a report on chemical analysis test results is read out of storage means by control means, processed, edited, and output only by designating any one of a request form number, an analytical measurement test sample identification number, an analytical measurement test sample acceptance date and an analytical measurement test sample group name and specifying a request form for preparing the report on chemical analysis test results. Therefore, during preparation for a report on chemical analysis test results, hands are usually unnecessary except the operation for specifying a request form as described above and an accurate report on chemical analysis test results can be prepared quickly.

(2) The reliability of analysis results is improved.

As described above, a report on chemical analysis test results is usually automatically prepared by control means and storage means.

For example, the processing for rounding off a value for obtaining a final result to be entered in a report on chemical analysis test results is executed by automatically reading the information for the lower limit value and the number of significant digits an analytical measurement test previously defined by an analytical measurement test sample group, analytical measurement test item, and analytical measurement test method out of storage means by control means. That is to say, because the processing is automatically executed without hands, the number of errors due to hands such as data transfer errors is decreased to zero and moreover, the processing such as rounding-off is always executed according to the same criterion for each analytical measurement test sample group, analytical measurement test item, and analytical measurement test method, and thereby a report on chemical analysis test results is prepared. Therefore, the reliability of analysis results is improved.

(3) Analytical measurement test results can effectively be used.

It is possible to read and transfer a report on chemical analysis test results on-line via a network. Therefore, in the case of a customer such as the manufacturing department, transferred analytical measurement test results can quickly be used for the quality control of a raw material on-line by immediately plotting the results in a raw-material quality control chart and resultingly, the results can be used to improve the quality control accuracy, product quality, and productivity. Moreover, because a report on analysis results is accelerated, analytical measurement test results are quickly be reflected on acceptance of a raw material or the like, the raw-material utilization factor is improved because a stored quantity of raw materials and a storing space are reduced, and the advantage of cost reduction or the like is obtained.

(4) An analysis information keeping space can be reduced.

Because every piece of analysis information necessary for a chemical analysis measurement test is made electronic and controlled and processed by a computer, an analysis information keeping space can be reduced.

Thus, the present system can provide chemical analysis test results with a very high reliability for a customer. Therefore, the manufacturing department serving as a customer of this embodiment can obtain the advantages that the quality control accuracy is improved, the raw-material utilization factor is improved, and costs are reduced.

Figure 9:
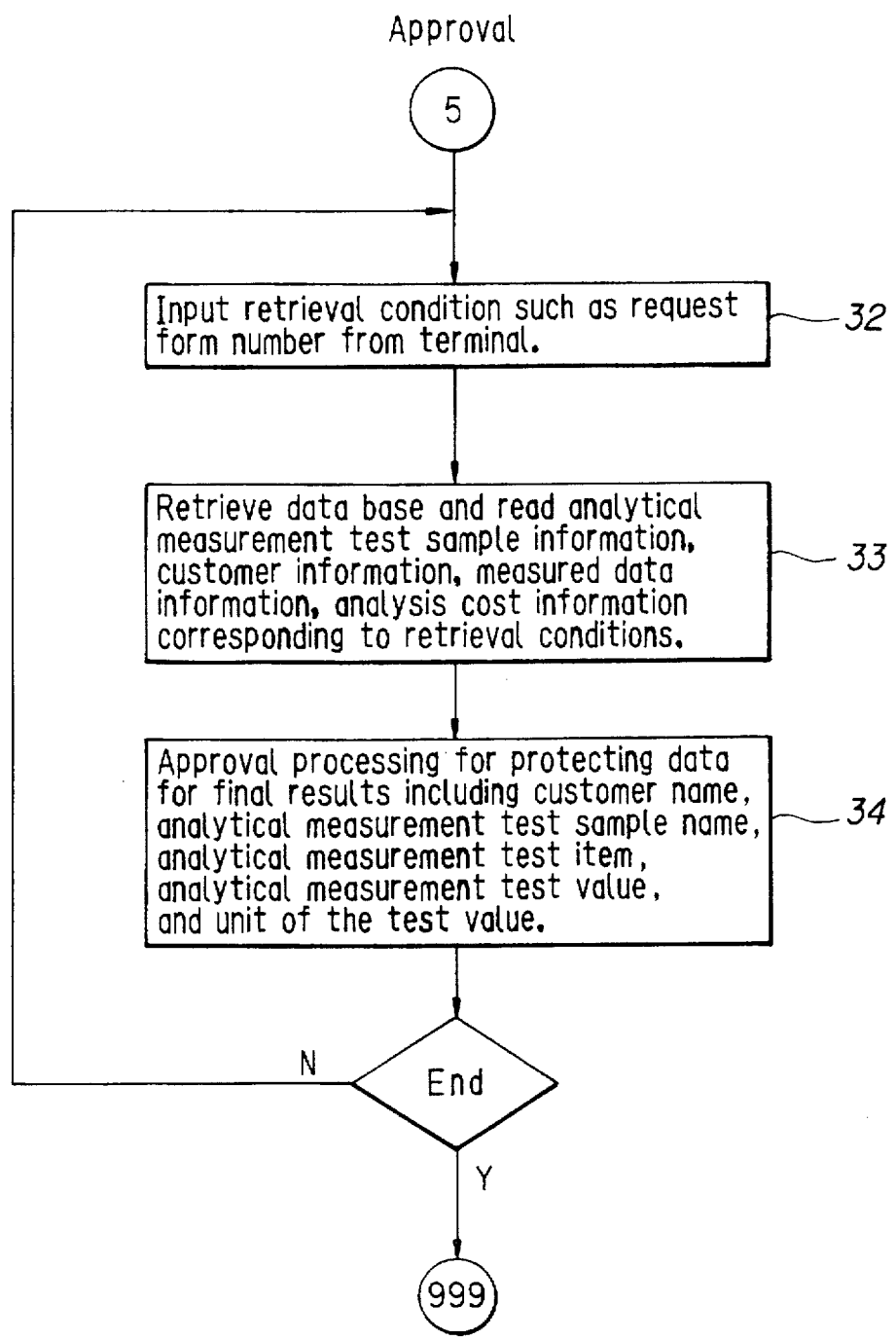
FIG. 9 is a flow chart showing the sequence of "approval" processing.
Figure 10:
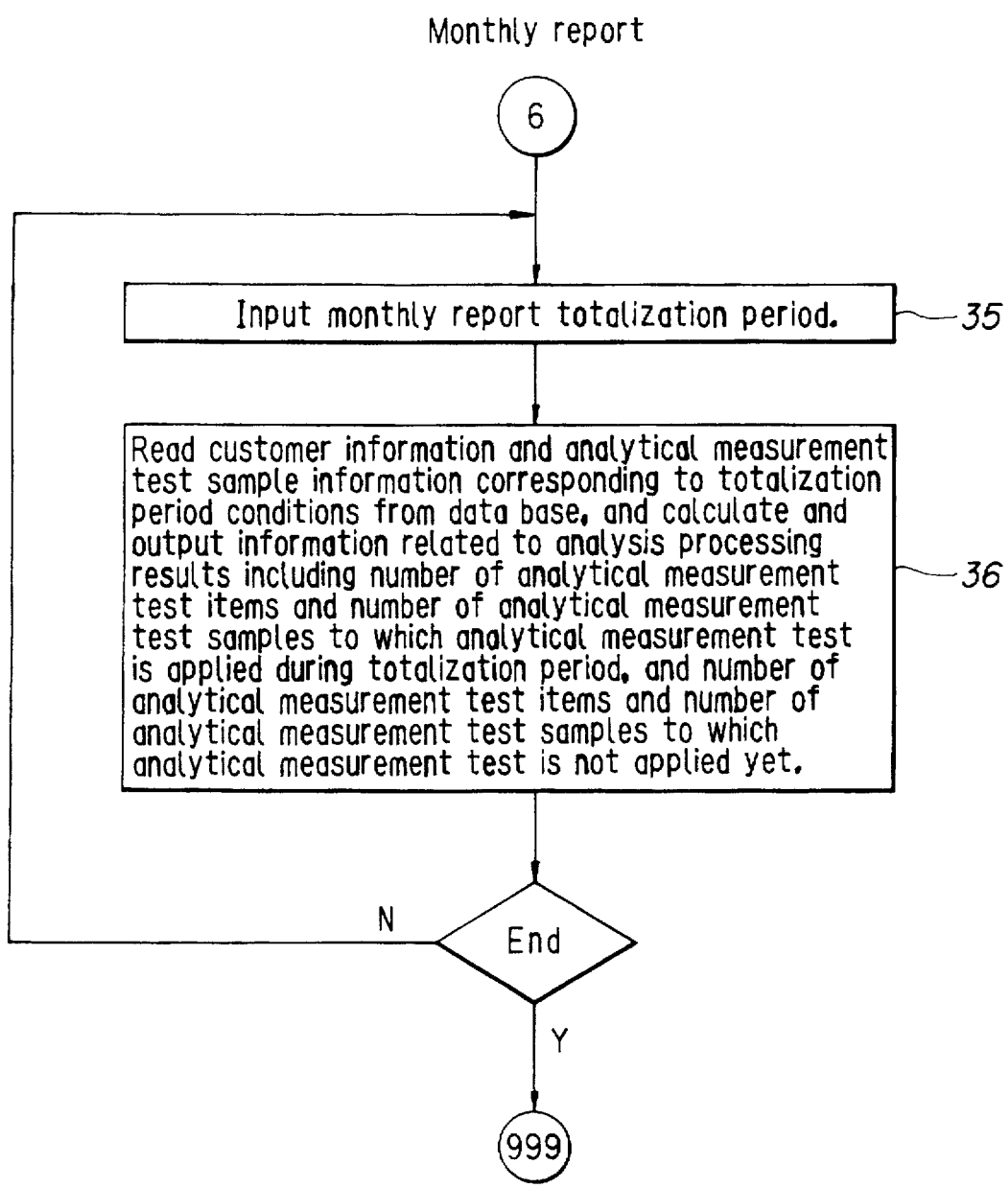
FIG. 10 is a flow chart showing the sequence of "monthly report" processing.
Figure 11:
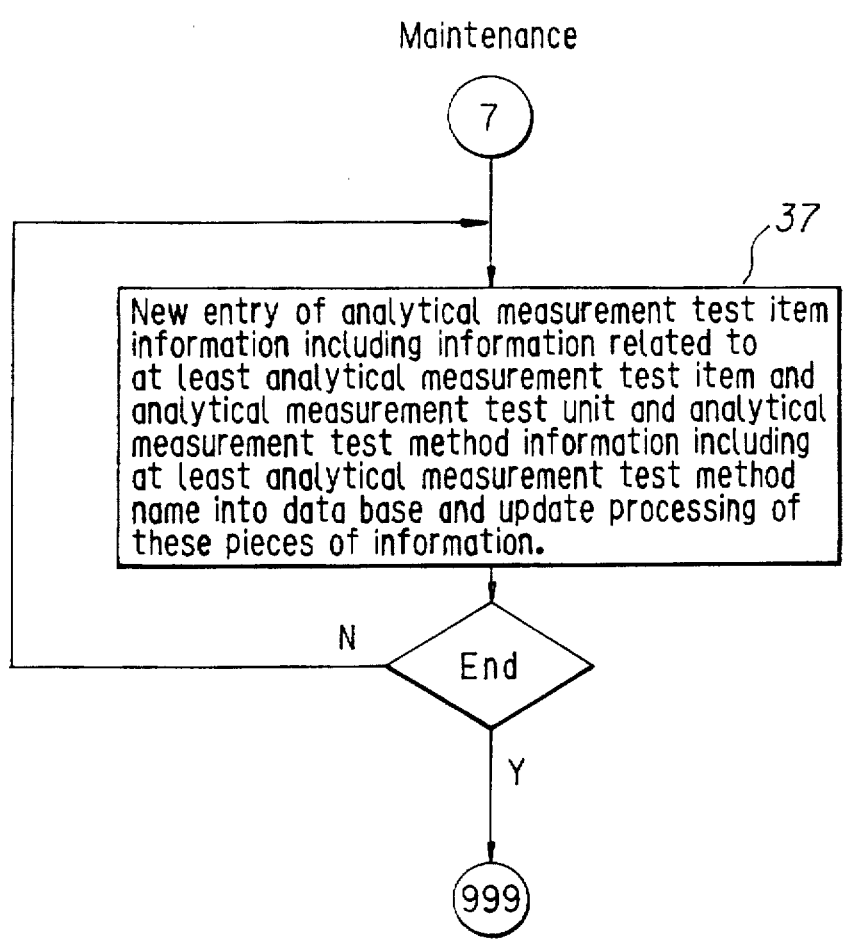
FIG. 11 is a flow chart showing the sequence of "maintenance" processing.

Because this embodiment further improves and secures the reliability of chemical analysis test results even if a report on chemical analysis test results is prepared, it inhibits an outsider from accessing a report on chemical analysis test results until the "approval" processing for the report on chemical analysis test results is completed by a responsible person in the chemical analysis department. FIG. 9 shows an example of the approval processing. A customer can read, output, or use chemical analysis test results after the "approval" processing is completed. Moreover, it is possible to transfer the report on chemical analysis test results to a customer by an electronic mail or automatic facsimile.

The "approval" processing is executed by clicking "approval", for example, clicking the request form number with which the report on chemical analysis test results is prepared with a mouse (steps 32 to 34). It is also possible to "approve" the reports on chemical analysis test results which are not approved yet collectively. The reports on chemical analysis test results undergoing the "approval" processing are protected but any report entry cannot be added, deleted, or changed.

Because the system of this embodiment makes it possible to read or transfer a report on chemical analysis test results on-line via a network, the manufacturing department can quickly use a report on chemical analysis test results approved by the chemical analysis department for the quality control of raw materials by immediately plotting chemical analysis results in a raw-material quality control chart. Moreover, the results are effectively used to improve the product quality and the productivity.

Figure 15:
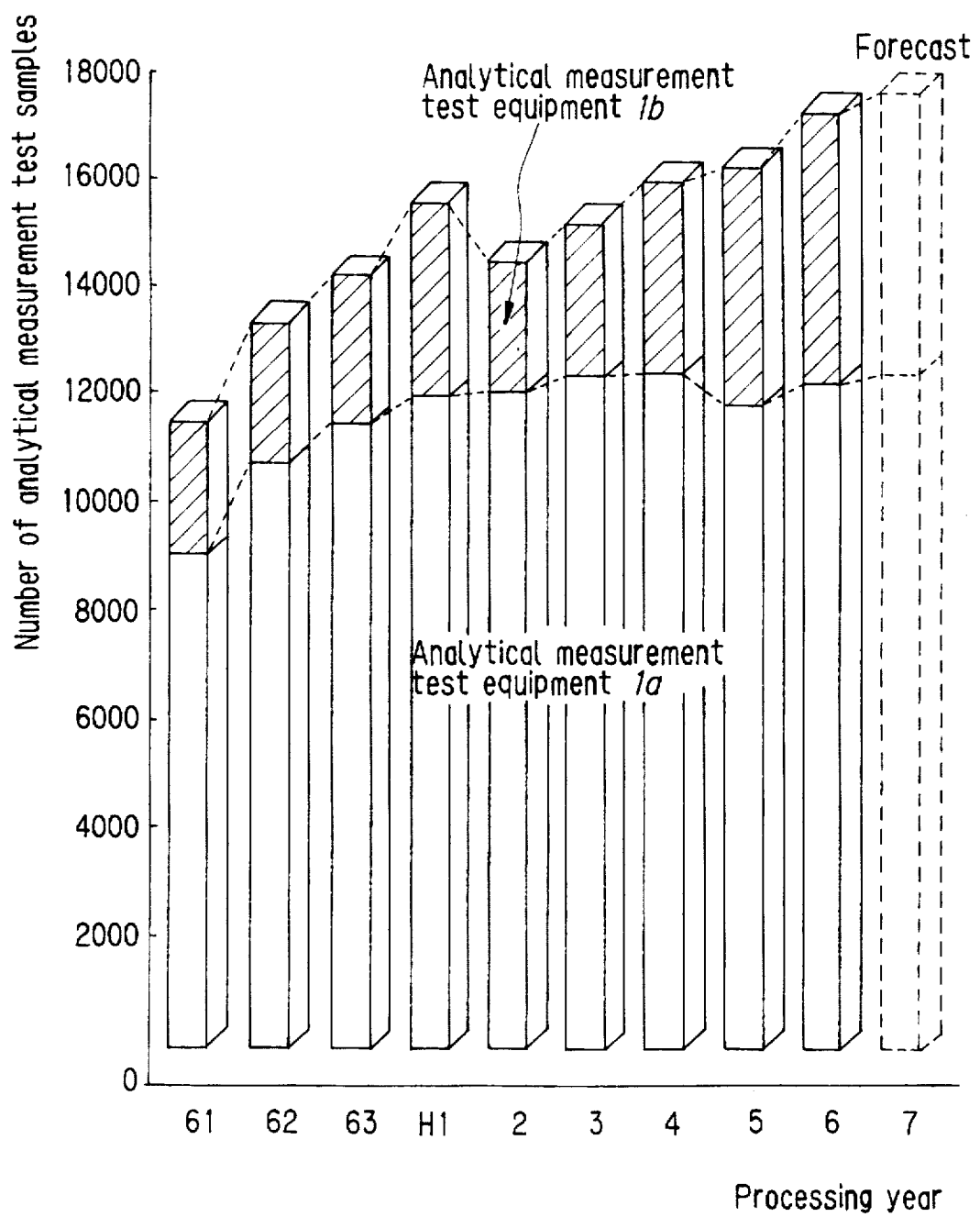
FIG. 15 is a graph showing an annual transition of the number of analytical measurement test samples.

Moreover, the system of this embodiment makes it possible to easily prepare a daily report, monthly report, quarterly report, and annual report. An example of the "monthly report" processing is shown by steps 35 and 36 in FIG. 10. The above reports serve as important materials for evaluation of results of the chemical analysis department, future personnel plan, and future equipment introduction plan. For example, FIG. 15 shows annual transition of the number of analytical measurement test samples used by analytical measurement test equipment. The graph in FIG. 15 can immediately be prepared by clicking "monthly report" with a mouse and inputting a necessary matter such as a retrieval range (step 36).

When new master information such as a new customer name, new analytical measurement test sample group related to a new analytical measurement test sample not included in any one of the already entered analytical measurement test sample groups, new analytical measurement test equipment, or new analytical measurement test method appears, the information is entered in the data base system before executing the "acceptance" processing. The entry or update processing of the new master information is performed by clicking "maintenance" in the main menu with a mouse, then designating the type of the master information, and inputting the master information (step 37). The master information is protected by the fact that the entry or update processing of the master information can be performed only by persons with a certain qualification. The master information is basic information for the present system to correctly function, which is used to eliminate errors and keep the consistency of information.

If there is master information not previously entered, it is not displayed in a selection window at the time of the "acceptance" processing of an analytical measurement test sample. Moreover, when the master information not entered is input, an error occurs. In this case, it is possible to continue the "acceptance" processing by clicking "maintenance" with a mouse, entering the new master information causing the error, and moving the mouse again to make the "acceptance" screen active.

Any one can execute the "acceptance" processing, but entry or update of master information requires a certain qualification (privilege) in order to protect information. Therefore, even after changing from the "acceptance" processing to the "maintenance" processing, a certain qualification is necessary for entry or update of the master information.

As described above, because the automatic system of this embodiment computerizes all chemical analysis test processes from acceptance and measurement of an analytical measurement test sample for the chemical analysis test to report on results, it has the advantage that the chemical analysis test can be executed accurately, very quickly, and smoothly at a high efficiency. Because the present system has a high reliability and a high instantaneousness of a chemical analysis test, the manufacturing department serving as a customer can improve, for example, the accuracy of raw-material quality control and the raw-material utilization factor and decrease the raw material stock. Therefore, the section can expect great advantages such as improvement of the product quality and improvement of the productivity.

Embodiment 2

Embodiment 2 of the present invention will be described with reference to a case of executing a chemical analysis test on unspecified analytical measurement test items like an analytical measurement test for research and development as an example.

In the case of this Embodiment 2, differences from Embodiment 1 will be mainly described.

The arrangement of analytical measurement test equipment having a control computer, a host computer exclusively used for a data base system, a work station serving as an input/output terminal, and a laser-beam printer in the automatic analysis system of this embodiment is almost the same as in Embodiment 1 shown in FIG. 1 and therefore, detailed description of the arrangement is omitted. However, the "manufacturing department" in FIG. 1 is replaced with "research and development section".

The processing sequence of the data base system from "acceptance" to "end" to be executed from a terminal is the same as in Embodiment 1. However, because an example of the arrangement form shown in FIG. 16 is different, it will be described below in more detail.

This arrangement form is an analysis arrangement form of an analytical measurement test sample for executing a wet chemical analysis test which is one of the analytical measurement test classifications. The following are entered in the arrangement form on an arrangement form output day: a request form number with which an analytical measurement test should be executed, an analysis requester's name which is a customer name, an analytical measurement test sample group name, an analytical measurement test sample name, analysis due date, analysis priority, the name of a person in charge of analysis, an analytical measurement test method name, and an analytical measurement test item name. Any analyst can obtain the information for the priority and analysis due date of an analytical measurement test sample and an analytical measurement test item assigned to the analyst and other analytical measurement test items, effectively use the information for analysis arrangement, and execute analysis accurately and smoothly. To output the arrangement form, "arrangement" in the main menu shown in FIG. 2 is first selected. When "analysis arrangement" screen opens, the type of arrangement form to be prepared is clicked with a mouse out of the displayed menu like, for example, "list of unanalyzed samples". Then, when inputting, for example, an analysis acceptance date as a retrieval item, the arrangement form shown in FIG. 16 is output.

An analyst executes a chemical analysis test in accordance with the arrangement form. This sequence is also the same as in Embodiment 1, but input of an analysis value to be executed from a terminal by manipulating a mouse will be described in more detail.

When clicking "analysis" in the main menu shown in FIG. 2 with a mouse, "analysis" screen is opened. Therefore, for example, a request form number is designated to click "analysis value input".

When analytical measurement tests of a plurality of analytical measurement test samples are requested by one request form, a selection window opens which displays a list of the samples entered in the request form. Therefore, a purposed analytical measurement test sample is selected by clicking it with a mouse. Then, when a selection window opens which displays a list of analytical measurement test items of the selected analytical measurement test sample, a purposed analytical measurement test item is selected by clicking it with the mouse. Then, when a window opens to which the analytical measurement test value of the selected analytical measurement test item is input, a measured-data input field is first clicked to input measured data.

When the analytical measurement test item to which the measured data is input is an analytical measurement test item previously stored in the master information of the analytical measurement test sample group of the analytical measurement test sample, the measured data is automatically rounded off in accordance with the master information and displayed in a report value input field. The value input to the report value input field is a value to be entered in a report on analysis results as final results to be mentioned later and numerical values and characters displayed in the field are directly entered in the report. In this case, when analysts or units are changed, a changed analyst or unit can be input through a selection window by operating a mouse. Finally, input information is confirmed on a screen, then it is designated to enter the information in the data base system, and the "analysis" processing is completed. The sequence of information input is described so that terminal operations can smoothly be progressed similarly to other processings. However, as a matter of course, the sequence is not restricted to this embodiment.

Figure 17:
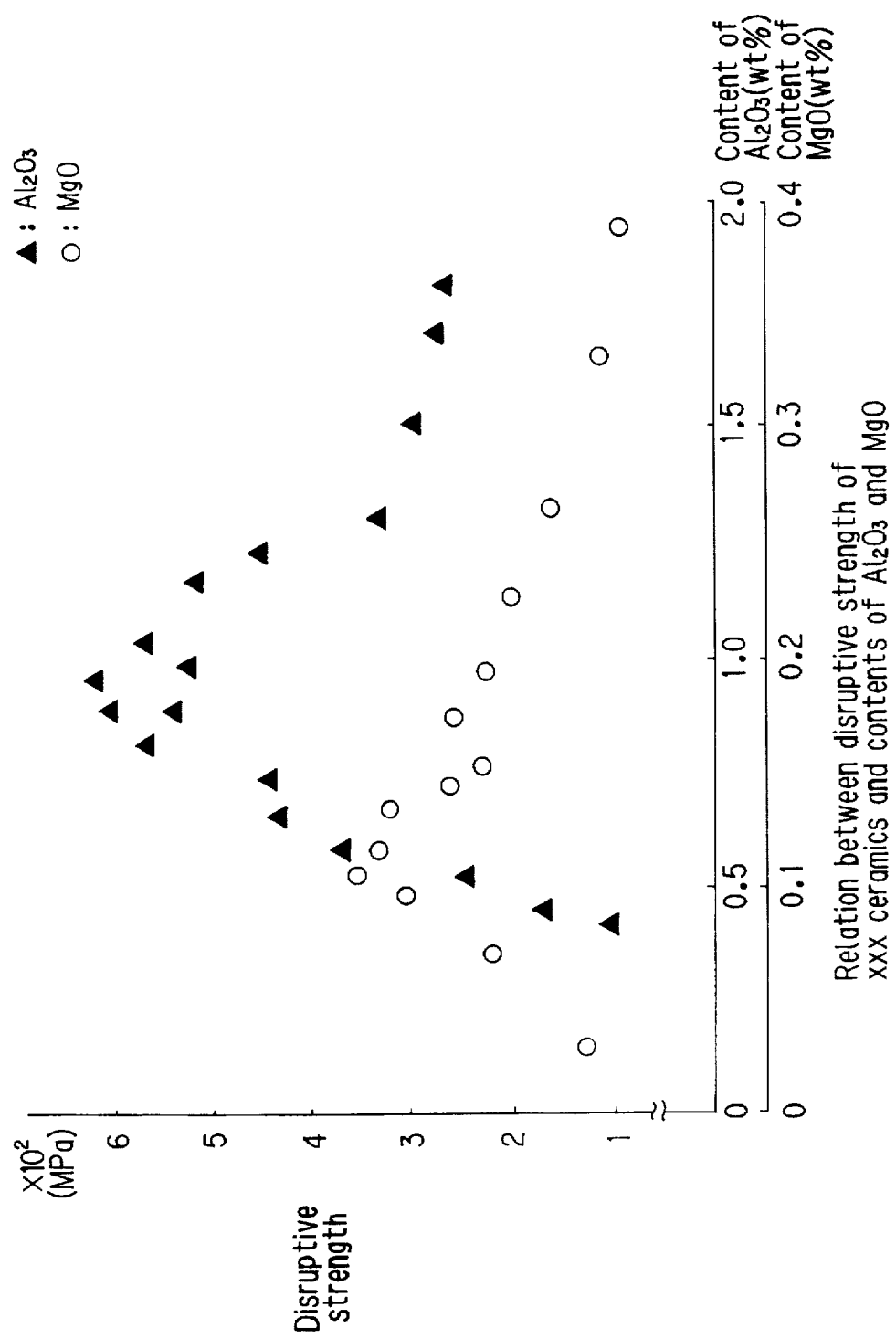
FIG. 17 is a graph showing data obtained from statistical analysis.

Because the system of this embodiment makes it possible to read and transfer a report on chemical analysis test results on-line via a network, the research and development section can immediately perform data processing such as statistical analysis shown in, for example, FIG. 17 in accordance with a report on chemical analysis test results approved by the chemical analysis department and use the processed data for improvement of the efficiency of research and development.

Figure 18:
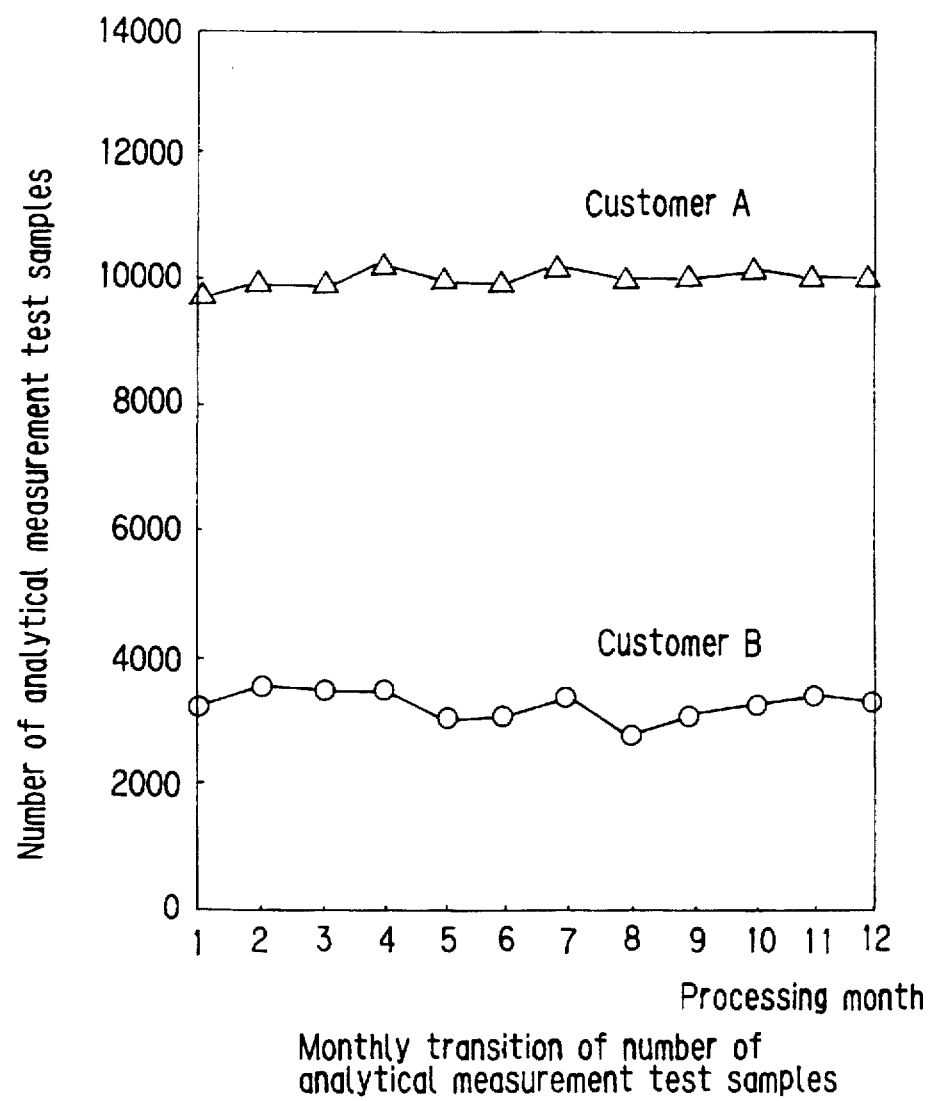
FIG. 18 is a graph showing monthly transition of the number of analytical measurement test samples of customer A and that of customer B.
Figure 19:
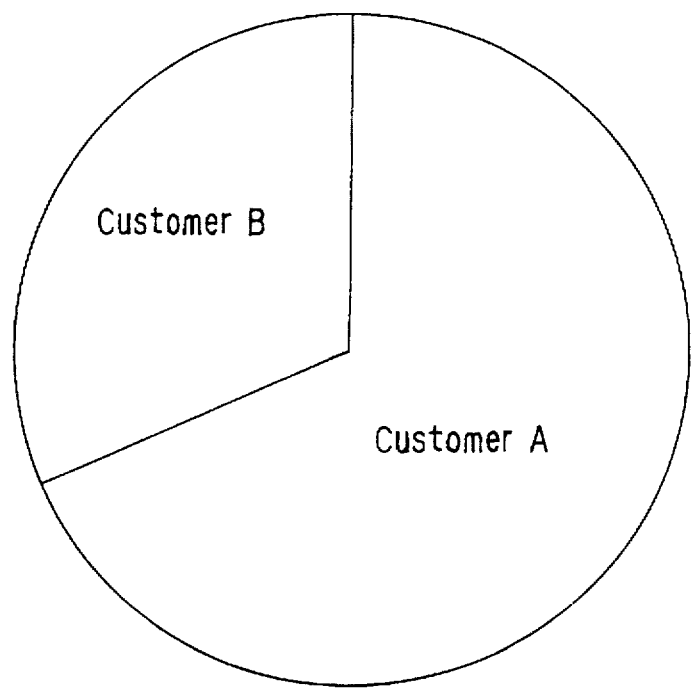
FIG. 19 is a graph showing a rate of annual number of analytical measurement test samples for each request department.

Moreover, the system of this embodiment makes it possible to easily prepare a daily report, monthly report, quarterly report, and annual report. These reports serve as important materials for evaluation of results of the chemical analysis department, future personnel plan, and future equipment introduction plan. For example, FIG. 18 shows monthly transition of the numbers of analytical measurement test samples of customers A and B and FIG. 19 shows a rate of the annual number of analytical measurement test samples for each request department. These materials can immediately be prepared by clicking "monthly report" in the main menu in FIG. 2 with a mouse and inputting a necessary matter such as a retrieval range.

Embodiment 3

Figure 20:
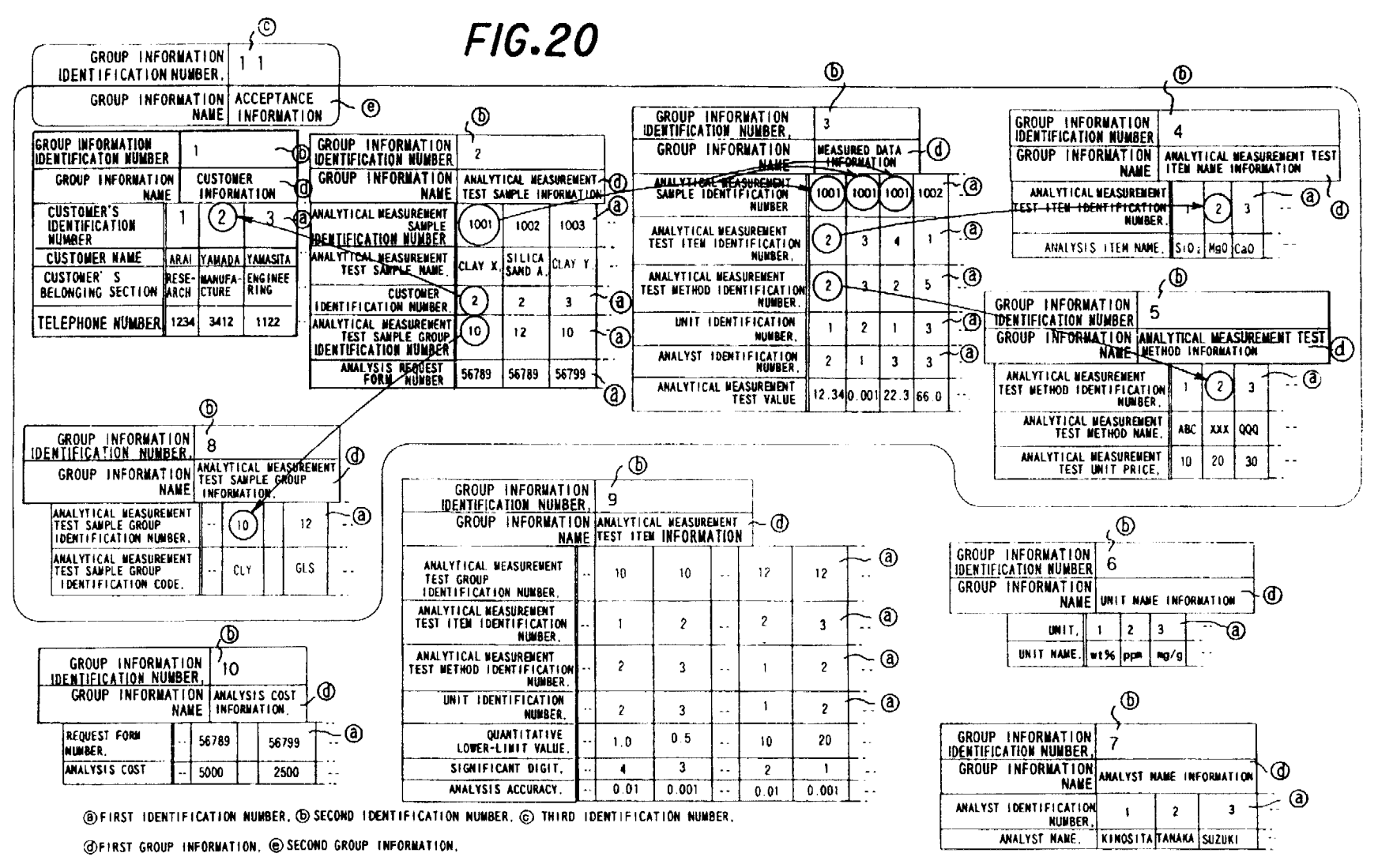

FIG. 20 shows "acceptance information" which is an example of related and grouped pieces of analysis information.

In FIG. 20, symbol (a) represents a first identification number, (b) represents a second identification number, (c) represents a third identification number, (d) represents first group information, and (e) represents second group information. As shown in FIG. 20, customer information (d) which belongs to the first group information comprises a plurality of customer identification numbers (1, 2, 3, ...) (a) which belong to the first identification number and is provided with the second identification number (b). Similarly, analytical measurement test sample information (b) which belongs to the first group information comprises a plurality of analytical measurement test sample identification numbers (1001, 1002, 1003, ...) and is provided with the second identification number (b). The same is applied to others.

In the case of these pieces of analysis information, as shown by arrows in FIG. 20, customer information, analytical measurement test sample information, measured data information, analytical measurement test item name information, analytical measurement test method information, and analytical measurement test sample group information which belong to the first group information (d) are respectively related to a customer identification number (e.g. 2), an analytical measurement test sample identification number (e.g. 1001), an analytical measurement test sample group identification number (e.g. 10), an analytical measurement test item identification number (e.g. 2) and an analytical measurement test method identification number (e.g. 2) of the first identification numbers (a) and grouped to form "acceptance information" which belongs to the second group information (e) and a third identification number (c) (in this case, 11) is given to the second group information (e).

Embodiment 4

FIG. 21 shows "analytical measurement test information" which is an example of related and grouped pieces of analysis information.

Types of the respective pieces of analysis information and the type of the first group information are the same as shown in FIG. 20, but second group information obtained by further grouping the first group information is different from that in FIG. 20.

In the case of the respective pieces of analysis information in FIG. 21, analytical measurement test item information, analytical measurement test method information, analytical measurement test sample group information, and analytical measurement test item information which belong to the first group information (d) are respectively related to an analytical measurement test item identification number (e.g. 1), an analytical measurement test method identification number (e.g. 2) and an analytical measurement test sample group identification number (e.g. 10) which belong to the first identification number (a) as shown by arrows and grouped to form the "analytical measurement test information" which belongs to the second group information (e) and a third identification number (c) (in this case, 12) is given to the second group information (e).

Embodiment 5

Figure 22:
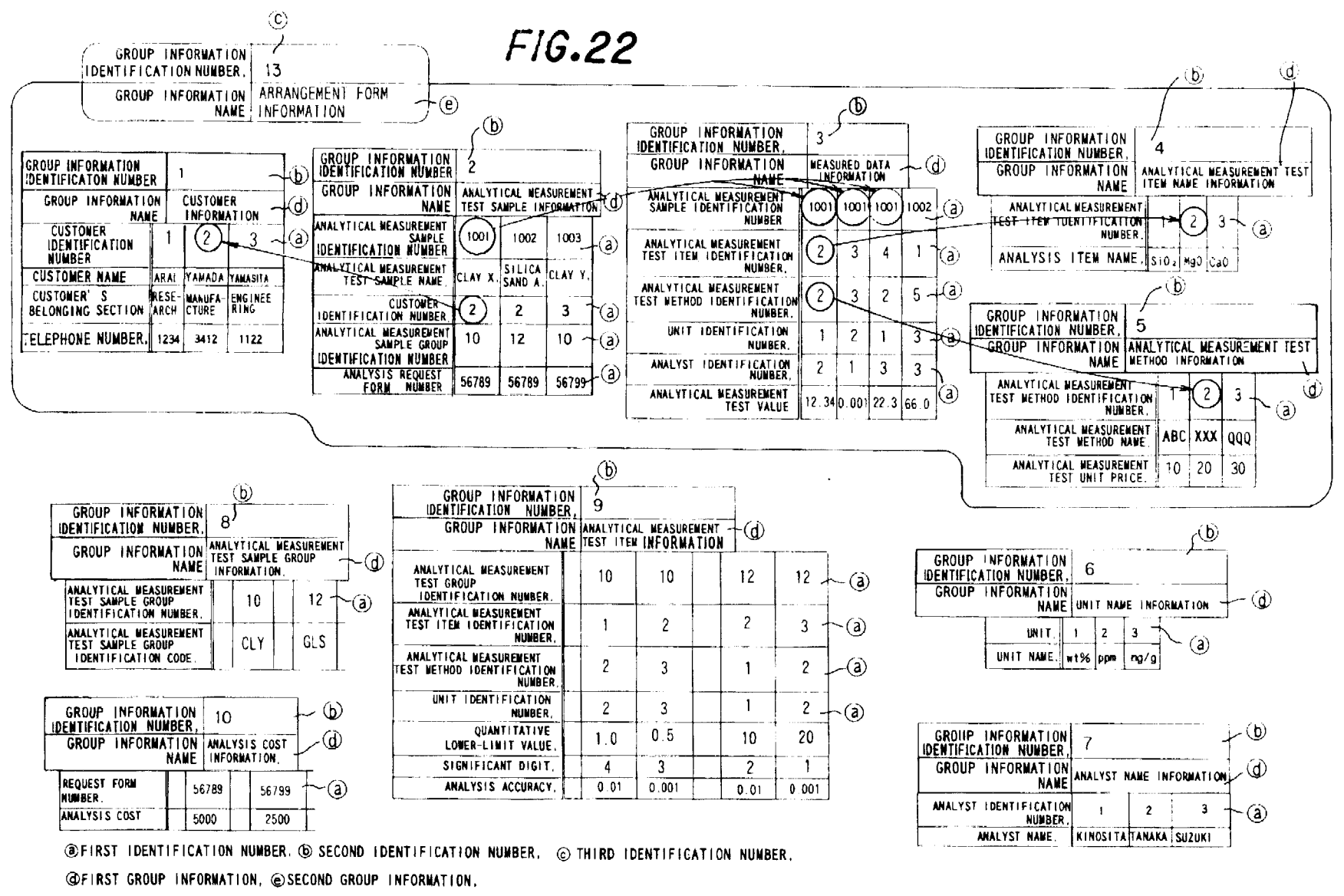

FIG. 22 shows "arrangement form information" which is an example of related and grouped pieces of analysis information.

Types of the respective pieces of analysis information and the type of he first group information are the same as in FIG. 20, but second group information obtained by further grouping the first group information is different from that in FIG. 20.

In the case of the respective pieces of analysis information in FIG. 22, as shown by arrows, customer information, analytical measurement test sample information, measured data information, analytical measurement test item name information, and analytical measurement test method information which belong to the first group information (d) are respectively related to a customer identification number (e.g. 2), an analytical measurement test sample identification number (e.g. 1001), an analytical measurement test method identification number (e.g. 2) and an analytical measurement test item identification number (e.g. 2) of the first identification numbers (a), and grouped to form the "arrangement form information" which belongs to the second group information (e) and a third identification number (c) (in this case, 13) is given to the second group information (e).

Embodiment 6

FIG. 23 shows "analysis progress information" which is an example of related and grouped pieces of analysis information.

Types of the respective pieces of analysis information and the type of the first group information are the same as in FIG. 20, but second group information obtained by further grouping the first group information is different from that in FIG. 20.

In the case of the respective pieces of analysis information in FIG. 23, as shown by arrows, customer information, analytical measurement test sample information, measured data information, analytical measurement test item name information, analytical measurement test method information, and unit name information which belong to the first group information (d) are respectively related to a customer identification number (e.g. 2), an analytical measurement test sample identification number (e.g. 1001), an analytical measurement test method identification number (e.g. 2), an analytical measurement test item identification number (e.g. 2) and a unit identification number (e.g. 1) of the first identification numbers (a) and grouped to form the "analysis progress information" which belongs to the second group information (e) and a third identification number (in this case, 14) is given to the second group information (e).

Embodiment 7

Figure 24:
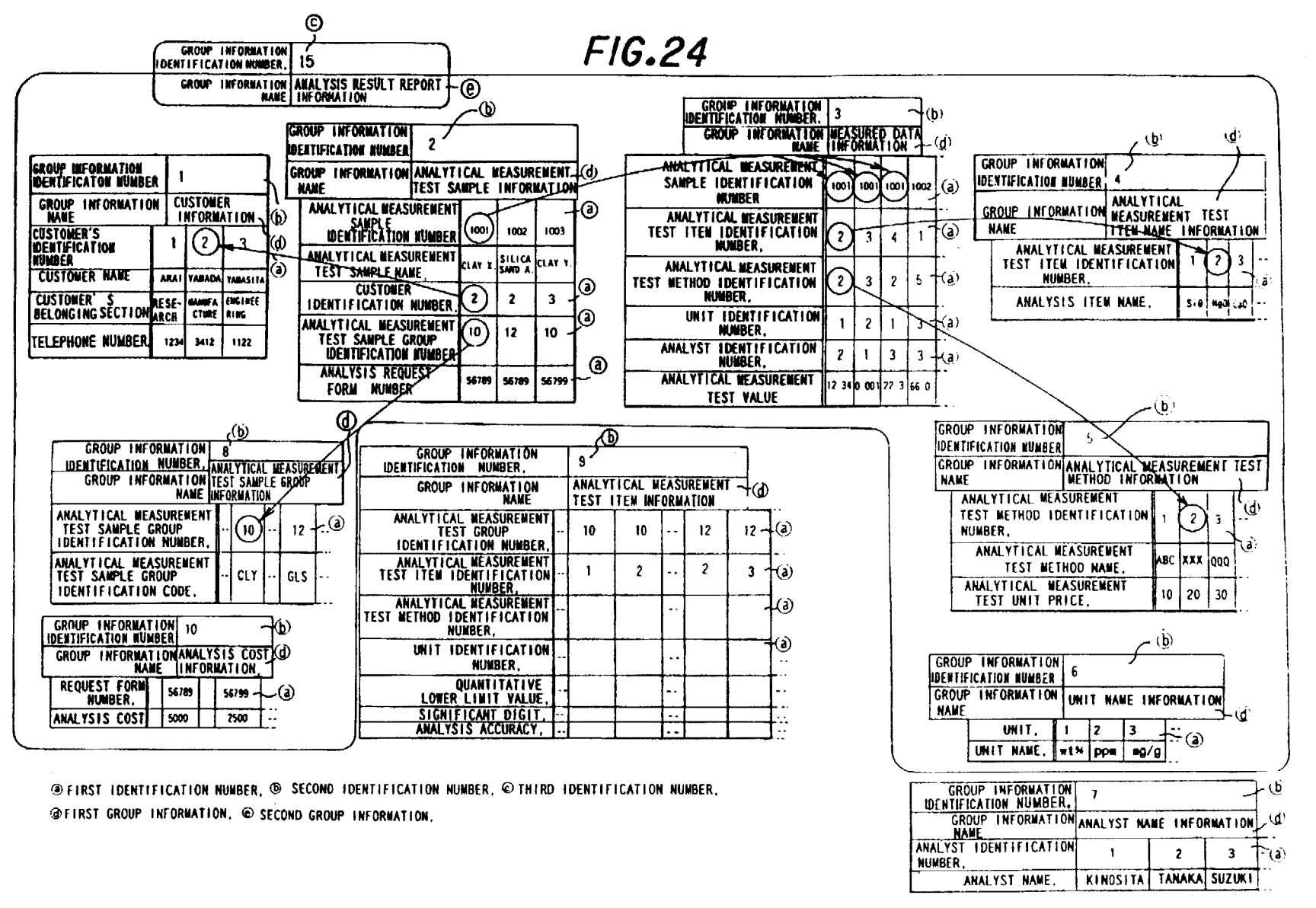

FIG. 24 shows "analysis result report information" which is an example of related and grouped pieces of analysis information.

Types of the respective pieces of analysis information and the type of the first group information are the same as in FIG. 20, but second group information obtained by further grouping the first group information is different from that in FIG. 20.

In the case of the respective pieces of analysis information in FIG. 24, as shown by arrows, customer information, analytical measurement test sample information, measured data information, analytical measurement test item name information, analytical measurement test method information, unit name information, analytical measurement test sample group information, and analysis cost information which belong to the first group information (d) are respectively related to a customer identification number (e.g. 2), an analytical measurement test item identification number (e.g. 2), a unit identification number (e.g. 1), an analytical measurement test item identification number (e.g. 2), a unit identification number (e.g. 1), an analytical measurement test sample group identification number (e.g. 10) and an analysis request form number (e.g. 56789), and grouped to form the "analysis result report information" which belongs to the second group information (e) and a third identification number (c) (in this case, 15) is given to the second group information (e).

As shown in FIGS. 20 to 24 (Embodiments 3 to 7), an identification number is individually given to each piece of analysis information and, not only a predetermined number of analysis information are grouped and provided with an identification number but also a predetermined number of pieces of analysis information necessary for a desired test result report are grouped for each predetermined viewpoint and provided with an identification number to store the grouped pieces of analysis information. Therefore, it is possible not only to process the pieces of analysis information at a high efficiency and a high speed but also to output the respective pieces of analysis information necessary for an analytical measurement test as an "arrangement form" before executing the analytical measurement test. Therefore, it is possible to execute the analytical measurement test correctly and smoothly without artificial errors and report very reliable test results. Moreover, an "analysis progress" state can be read in the middle stage of the analytical measurement test, the analytical measurement test can be controlled accurately and quickly, and moreover the analytical measurement test efficiency is improved.

What is claimed is:

1. An automatic analysis system comprising analytical equipment and a host computer connected thereto, said host computer comprising:

storage means for storing pieces of analysis information and group information, control means for (i) assigning identification numbers for identification to the pieces of analysis information, respectively, (ii) assigning identification numbers to the pieces of analysis information, respectively, to relate the pieces of analysis information to each other, (iii) grouping a predetermined number of the pieces of analysis information to form pieces of group information, (iv) assigning identification numbers to the pieces of group information, respectively, (v) further grouping a predetermined number of the pieces of group information to form pieces of group information, and (vi) assigning identification numbers to the pieces of group information, respectively, the control means further comprising means for retrieving the pieces of analysis information and group information stored in the storage means, reading same in a mutually related manner, processing and editing same, and outputting final processed and edited results via output means, wherein an analytical measurement test value in the final results is rounded off by at least one of the pieces of information directed to a lower limit value, an analysis accuracy and an output format designation of an analytical measurement test method corresponding to an analytical measurement test item.

2. The automatic analysis system according to claim 1 wherein the pieces of analysis information are grouped to a predetermined number in accordance with a common attribute.

3. The automatic analysis system according to claim 1 wherein the pieces of analysis information are grouped in accordance with any of a purpose of the pieces of analysis information as well as properties, a chemical composition and an analytical measurement test method of an analytical measurement test sample.

4. The automatic analysis system according to claim 1 wherein the pieces of analysis information comprise measured data and pieces of relevant information other than the measured data.

5. The automatic analysis system according to claim 4 wherein the relevant information comprises customer information including at least a customer name and analytical measurement test sample information including at least an analytical measurement test sample name.

6. The automatic analysis system according to claim 5 wherein in the analytical measurement test sample information, an analytical measurement test sample to which an identification number is given and which is recognized by an analytical measurement test sample name is related to one piece of sample group information among a plurality of pieces of analytical measurement test sample group information to which an identification number is given and which is recognized by an analytical measurement test sample group name, and the analytical measurement test sample group information is related to at least an analytical measurement test item corresponding to the analytical measurement test sample group name, and analytical measurement test item information including at least one of pieces of information regarding a lower limit value, an analysis accuracy and an analytical measurement test value output format designation of an analytical measurement test concerning an analytical measurement test method corresponding to the analytical measurement test item.

7. The automatic analysis system according to claim 6 wherein the analytical measurement test item information includes information regarding a unit of an analytical measurement test value corresponding to the analytical measurement test item.

8. The automatic analysis system according to claim 4 wherein the relevant information comprises analytical measurement test method information including at least an analytical measurement test method name.

9. The automatic analysis system according to claim 8 wherein the analytical measurement test method information includes information regarding at least one of an analytical measurement test unit cost corresponding to an analytical measurement test method to which an identification number is given and which is recognized by an analytical measurement test method name, and analytical measurement test unit costs corresponding to a plurality of analytical measurement test methods to which identification numbers are given and which are recognized by analytical measurement test method group names.

10. The automatic analysis system according to claim 1 wherein prior to the practice of an analytical measurement test, pieces of analysis information including at least one of a test item, a test sequence, a test method and test conditions necessary for the analytical measurement test are read out of the storage means by the control means, and then output as an arrangement form.

11. The automatic analysis system according to claim 1 wherein an analysis progress state in the middle stage of an analytical measurement test is read out of the storage means, and then inquired.

12. The automatic analysis system according to claim 1 wherein the final results include at least a customer name, an analytical measurement test sample name, an analytical measurement test item, an analytical measurement test value and a unit of the analytical measurement test value, and they are output in a uniform format.

13. The automatic analysis system according to claim 1 wherein the final results include information regarding a cost of an analytical measurement test for obtaining the final results.

14. The automatic analysis system according to claim 1 wherein at least one of an error range of the analytical measurement test value, a confidence limit and an analysis accuracy is written in the final results.

15. An automatic analysis system comprising an analytical equipment and a host computer connected thereto, said host computer comprising:

storage means for storing pieces of analysis information to which first, second and third identification numbers have been assigned, control means for (i) assigning first identification numbers to the pieces of analysis information, respectively, to mutually identify the pieces of analysis information and to relate the pieces of analysis information to each other, (ii) grouping a predetermined number of the pieces of analysis information to form pieces of first group information, (iii) assigning second identification numbers to the pieces of first group information, respectively, (iv) further grouping the pieces of first group information in accordance with a predetermined viewpoint to form pieces of second group information, and (v) assigning third identification numbers to the pieces of second group information, respectively, the control means further comprising means for retrieving the pieces of analysis information and group information stored in the storage means, reading same in a mutually related manner, processing and editing same, and outputting final processed and edited results via output means, wherein an analytical measurement test value in the final results is rounded off by at least one of pieces of information directed to a lower limit value, an analysis accuracy and an output format designation of an analytical measurement test method corresponding to an analytical measurement test item.

16. A method of processing data in an automatic analysis system, comprising the steps of:

inputting, into the automatic analysis system, at least an analytical measurement test sample name, a customer name, and an analytical measurement item name;

grouping, as analytical measurement test sample information, corresponding to first group information, (i) the analytical measurement test sample name and (ii) a customer identification number corresponding to the customer name stored in and retrieved from a customer information database;

assigning to the analytical measurement test sample information corresponding to the first group information an analytical measurement test sample identification number; and storing the analytical measurement test sample information and analytical measurement test sample identification number in a storage means.

17. The method of claim 16, further comprising:

retrieving analytical measurement test item name information corresponding to the analytical measurement test item name to obtain an analytical measurement test item identification number; and grouping (i) the analytical measurement test item identification number and (ii) the analytical measurement test sample identification number to obtain measured data information; and storing the measured data information in the storage means.

18. The method of claim 17, further comprising:

inputting from a terminal an analysis request form number corresponding to a piece of information for preparing a form arrangement; and retrieving from the storage means the piece of information for preparing a form arrangement.

19. The method of claim 18, further comprising:

retrieving, based on the request form number, the analytical measurement test sample information to obtain the analytical measurement test sample name, the analytical measurement test sample identification number, and the customer identification number.

20. The method of claim 17, further comprising:

retrieving the measured data information to obtain the analytical measurement test item identification number and an analytical measurement test method identification number, corresponding to the analytical measurement test sample identification number.

21. The method of claim 17, further comprising:

retrieving the analytical measurement test item name information to obtain an analytical item name corresponding to the analytical measurement test item identification number.

22. The method of claim 17, further comprising:

formatting the analytical measurement test sample name, the customer name, the analytical measurement item name and the analytical measurement test sample name; and outputting a formatted analytical measurement test sample name, customer name, analytical measurement item name and analytical measurement test sample name.

23. The method of claim 20, further comprising:

retrieving the analytical measurement test method information to obtain an analytical measurement test method name corresponding to the analytical measurement test method identification number.

24. The method of claim 20, further comprising:

relating an analytical measurement test value to the analytical measurement test sample identification number, the analytical measurement test item identification number and the analytical measurement test method identification number; and storing, on or off-line, the analytical measurement test value with the measured data information.

25. The method of claim 24, further comprising:

inputting from a terminal a request form number corresponding to a piece of information comprising information for preparing an analytical result report form; and retrieving the piece of information from the storage means.

26. The method of claim 25, further comprising:

retrieving, based on the input request from number, the analytical measurement test sample information to read the analytical measurement test sample name, the analytical measurement test sample identification number, the customer identification number, and the analytical measurement test sample group identification number.

27. The method of claim 26, further comprising:

retrieving customer information to obtain the customer name corresponding to the customer identification number.

28. The method of claim 26, further comprising:

retrieving, based on the analytical measurement test sample identification number, the measured data information to obtain the analytical measurement test value, the analytical measurement test item identification number, and the analytical measurement test method identification number.

29. The method of claim 26, further comprising:

retrieving the analytical measurement test item name information to obtain the analytical item name corresponding to the analytical measurement test item identification number.

30. The method of claim 26, further comprising:

retrieving the analytical measurement test method information to obtain the analytical measurement test method name corresponding to the analytical measurement test method identification number.

31. The method of claim 26, further comprising:

retrieving, based on the (i) analytical measurement test sample group identification number, (ii) analytical measurement test item identification number and (iii) the analytical measurement test method identification number, the analytical measurement test item information to obtain a unit identification number, a quantitative lower limit value and a number of significant digits.

32. The method of claim 31, further comprising:

retrieving, based on the unit identification number, unit name information to obtain a unit name corresponding to the unit identification number.

33. The method of claim 31, further comprising:

comparing the analytical measurement test value with the quantitative lower limit value; and displaying on a terminal whether a final report value is not more than the quantitative lower limit value when the analytical measurement test value is lower than the quantitative lower limit.

34. The method of claim 31, further comprising:

rounding off the analytical measurement test value in accordance with the number of significant digits; and outputting a final report value.

35. The method of claim 34, further comprising:

formatting the analytical measurement test sample, the customer name, the analytical item name, the final report value and the unit value; and outputting the analytical measurement test sample, the customer name, the analytical item name, the final report value and the unit value in a formatted form as an analytical results report.

* * * * *